United States Patent
Nantermet et al.

[11] Patent Number: 5,817,822
[45] Date of Patent: *Oct. 6, 1998

[54] CERTAIN ALPHA-AZACYCLOALKYL SUBSTITUTED ARYLSULFONAMIDO ACETOHYDROXAMIC ACIDS

[75] Inventors: Philippe G. Nantermet, Maplewood; David T. Parker, Livingston; Lawrence J. MacPherson, Hampton, all of N.J.

[73] Assignee: Novartis Corporation, Summit, N.J.

[ * ] Notice: The term of this patent shall not extend beyond the expiration date of Pat. No. 5,552,419.

[21] Appl. No.: 787,730

[22] Filed: Jan. 24, 1997

Related U.S. Application Data

[63] Continuation-in-part of Ser. No. 475,166, Jun. 7, 1995, Pat. No. 5,646,167, which is a continuation-in-part of Ser. No. 333,676, Nov. 3, 1994, Pat. No. 5,552,419, which is a continuation-in-part of Ser. No. 265,296, Jun. 24, 1994, Pat. No. 5,506,242.

[51] Int. Cl.$^6$ ................................................. C07D 401/02
[52] U.S. Cl. .................... 546/194; 546/186; 546/190; 546/192; 546/207
[58] Field of Search ........................ 546/186, 190, 546/192, 194, 207

[56] References Cited

U.S. PATENT DOCUMENTS

| | | | |
|---|---|---|---|
| 5,455,258 | 10/1995 | MacPherson et al. | 514/357 |
| 5,506,242 | 4/1996 | MacPherson et al. | 514/336 |
| 5,552,419 | 9/1996 | MacPherson et al. | 514/357 |

FOREIGN PATENT DOCUMENTS

| | | |
|---|---|---|
| 0606046 | 7/1994 | European Pat. Off. . |
| 9535276 | 12/1995 | WIPO . |
| 9600214 | 1/1996 | WIPO . |
| 9627583 | 9/1996 | WIPO . |

*Primary Examiner*—Zinna Northington Davis
*Attorney, Agent, or Firm*—Norbert Gruenfeld

[57] ABSTRACT

The present invention relates to the alpha-(N-substituted pyrrolidinyl and piperidinyl) alpha-(arysulfonamido)-acetohydroxamic acids of formula I

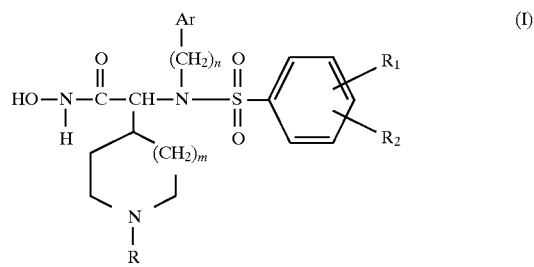

wherein R represents acyl derived from a carboxylic acid, from a carbonic acid or from a carbamic acid; or R represents (lower alkyl, aryl-lower alkyl or aryl)-sulfonyl, di-(aryl-lower alkyl or alkyl)-aminosulfonyl, or aryl-lower alkyl; Ar represents carbocyclic aryl, heterocyclic aryl or biaryl; $R_1$ and $R_2$ represent independently hydrogen, lower alkyl, lower alkoxy, halogen, hydroxy, acyloxy, lower alkoxy-lower alkoxy, trifluoromethyl or cyano; or $R_1$ and $R_2$ together on adjacent carbon atoms represent lower alkylenedioxy; m represents zero or one; n represents an integer from 1 to 5; pharmaceutically acceptable prodrug derivatives thereof; and pharmaceutically acceptable salts thereof; further to a process for the preparation of these compounds, to pharmaceutical compositions comprising these compounds, to the use of these compounds for the therapeutic treatment of the human or animal body or for the manufacture of a pharmaceutical composition.

20 Claims, No Drawings

CERTAIN ALPHA-AZACYCLOALKYL SUBSTITUTED ARYLSULFONAMIDO ACETOHYDROXAMIC ACIDS

CROSS-REFERENCE TO RELATED APPLICATIONS

This application is a continuation-in-part of application Ser. No. 08/475,166 filed Jun. 7, 1995, now U.S. Pat. No. 5,646,167 which is a continuation-in-part of application No. 08/333,676, filed Nov. 3, 1994, Now U.S. Pat. No. 5,552,419, which is a continuation-in-part application of application Ser. No. 08/265,296, filed Jun. 24, 1994, now U.S. Pat. No. 5,506,242, all of which are incorporated herein by reference.

SUMMARY OF THE INVENTION

The present invention relates to novel alpha-(N-substituted pyrrolidinyl and piperidinyl)-alpha-arylsulfonamido acetohydroxamic acids and derivatives described below, as inhibitors of matrix-degrading metalloproteinases and of TNF-alpha (tumor necrosis factor alpha) activity, methods for preparation thereof, pharmaceutical compositions comprising said compounds, a method of inhibiting TNF-alpha and matrix degrading metalloproteinase activity and a method of treating TNF-alpha and matrix metalloproteinase dependent diseases or conditions in mammals which are responsive to matrix metalloprotease and TNF-alpha inhibition, using such compounds or pharmaceutical compositions comprising such compounds of the invention.

The compounds of the invention are inhibitors of TNF-alpha converting enzyme (TNF-alpha convertase) and thus inhibit TNF alpha activity, e.g. suppress the production and/or release of TNF alpha, an important mediator of inflammation and tissue growth. Such properties render the compounds of the invention primarily useful for the treatment of tumors (malignant and non-malignant neoplasma) as well as of inflammatory conditions in mammals, e.g. for the treatment of arthritis (such as rheumatoid arthritis), septic shock, inflammatory bowel disease, Crohn's disease and the like.

The compounds of the invention also inhibit matrix degrading metalloproteinases such as gelatinase, stromelysin, collagenase, and macrophage metalloelastase. Thus the compounds of the invention inhibit matrix degradation and are also useful for the prevention or treatment of gelatinase-, stromelysin-, collagenase- and macrophage metalloelastase-dependent pathological conditions in mammals. Such conditions include tumors (by inhibiting tumor growth, tumor metastasis, tumor progression or invasion and/or tumor angiogenesis), such tumors being e.g. breast, lung, bladder, colon, ovarian and skin cancer. Other conditions to be treated with the compounds of the invention include osteoarthritis, bronchial disorders (such as asthma by inhibiting the degradation of elastin), atherosclerotic conditions (by e.g. inhibiting rupture of atherosclerotic plaques), as well as acute coronary syndrome, heart attacks (cardiac ischemia), strokes (cerebral ischemias), and restenosis after angioplasty, and also vascular ulterations, ectasia and aneurysms.

Further conditions to be treated with the compounds of the invention are inflammatory demyelinating disorders of the nervous system in which myelin destruction or loss is involved (such as multiple sclerosis), optic neuritis, neuromyelitis optica (Devic's disease), diffuse and transitional sclerosis (Schilder's disease) and acute disseminated encephalomyelitis, also demyelinating peripheral neuropathies such as Landry-Guillain-Barre-Strohl syndrome for motor defects; also tissue ulceration (e.g. epidermal and gastric ulceration), abnormal wound healing, periodontal disease, bone disease (e.g. Paget's disease and osteoporosis).

Ocular applications of the compounds of the invention include the treatment of ocular inflammation, corneal ulcerations, pterygium, keratitis, keratoconus, open angle glaucoma, retinopathies, and also their use in conjunction with refractive surgery (laser or incisional) to minimize adverse effects.

DETAILED DESCRIPTION OF THE INVENTION

The present invention relates to the alpha-(N-substituted pyrrolidinyl and piperidinyl) alpha-(arysulfonamido)-acetohydroxamic acids of formula I

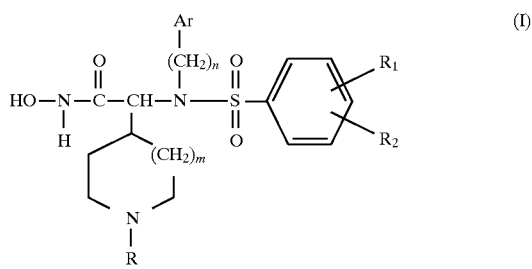

wherein
R represents acyl derived from a carboxylic acid, from a carbonic acid or from a carbamic acid; or R represents (lower alkyl, aryl-lower alkyl or aryl)-sulfonyl, di-(aryl-lower alkyl, aryl or alkyl)-aminosulfonyl, or aryl-lower alkyl;

Ar represents carbocyclic aryl, heterocyclic aryl or biaryl;

$R_1$ and $R_2$ represent independently hydrogen, lower alkyl, lower alkoxy, halogen, hydroxy, acyloxy, lower alkoxy-lower alkoxy, trifluoromethyl or cyano; or $R_1$ and $R_2$ together on adjacent carbon atoms represent lower alkylenedioxy;

m represents zero or one;

n represents an integer from 1 to 5;

pharmaceutically acceptable prodrug derivatives thereof; and pharmaceutically acceptable salts thereof; further to a process for the preparation of these compounds, to pharmaceutical compositions comprising these compounds, to the use of these compounds for the therapeutic treatment of the human or animal body or for the manufacture of a pharmaceutical composition.

The compounds of the invention depending on the nature of the substituents, possess one or more asymmetric carbon atoms. The resulting diastereoisomers, enantiomers and geometric isomers are encompassed by the instant invention.

Preferred are compounds wherein m represents one.

Preferred are the said compounds of the invention wherein the configuration of the asymmetric carbon atom of the α-aminohydroxamic acid moiety to which is attached the pyrrolidine or piperidine ring corresponds to that of a D-amino acid precursor and is assigned the (R)-configuration.

Pharmaceutically acceptable prodrug derivatives are those that may be convertible by solvolysis or under physiological conditions to the free hydroxamic acids of the invention and represent such hydroxamic acids in which the CONHOH group is derivatized in form of an O-acyl or an optionally substituted O-benzyl derivative. Preferred are the optionally substituted O-benzyl derivatives.

Prodrug acyl derivatives are preferably those derived from an organic carbonic acid, an organic carboxylic acid or a carbamic acid.

An acyl derivative which is derived from an organic carboxylic acid is, for example, lower alkanoyl, phenyl-lower alkanoyl or carbocyclic or heterocyclic aroyl, such as benzoyl or nicotinoyl.

An acyl derivative which is derived from an organic carbonic acid is, for example, alkoxycarbonyl, especially lower alkoxycarbonyl, which is unsubstituted or substituted by carbocyclic or heterocyclic aryl, or is cycloalkyloxycarbonyl, especially $C_3$–$C_7$-cycloalkyloxycarbonyl, which is unsubstituted or substituted by lower alkyl, or is alkoxycarbonyl which is substituted by biaryl, adamantyl, cycloalkyl, bicycloalkyl, lower alkoxy, phthalimido, 1,4-benzoxazin-3-onyl, benzoxazolonyl, amino, mono- or di-lower alkylamino, piperazino, N-lower alkylpiperazino, N-(carbocyclic or heterocyclic aryl-lower alkyl)piperazino, morpholino, thiomorpholino, piperidino, pyrrolidino, piperidinyl or N-lower alkylpiperidinyl, hexahydroazepino, hexahydroazepinyl or N-lower alkylhexahydroazepinyl, N-tetrahydroquinolinyl, N-tetrahydroisoquinolinyl, or by tetrahydropyranyl or tetrahydrofuranyl.

An acyl derivative which is derived from a carbamic acid is, for example, amino-carbonyl which is mono- or di-substituted by lower alkyl, carbocyclic or heterocyclic aryl-lower alkyl, carbocyclic or heterocyclic aryl, lower alkylene or lower alkylene interrupted by O or S.

Prodrug optionally substituted O-benzyl derivatives are preferably benzyl or benzyl mono-, di-, or tri-substituted by e.g. lower alkyl, lower alkoxy, amino, nitro, halogen and/or trifluoromethyl.

Pharmaceutically acceptable salts of the acidic compounds of the invention are salts formed with bases, namely cationic salts such as alkali and alkaline earth metal salts, such as sodium, lithium, potassium, calcium, magnesium, as well as ammonium salts, such as ammonium, trimethylammonium, diethylammonium, and tris-(hydroxymethyl)-methylammonium salts.

Similarly acid addition salts, such as of mineral acids, organic carboxylic and organic sulfonic acids e.g. hydrochloric acid, methanesulfonic acid, maleic acid, are also possible provided a basic group, such as pyridyl, constitutes part of the structure.

The general definitions used herein have the following meaning within the scope of the present invention, unless otherwise specified.

The term "lower" referred to above and hereinafter in connection with organic radicals or compounds respectively defines such as branched or unbranched with up to and including 7, preferably up to and including 4, and advantageously one or two carbon atoms.

A lower alkyl group is branched or unbranched and contains 1 to 7 carbon atoms, preferably 1–4 carbon atoms, and represents for example methyl, ethyl, propyl, butyl, isopropyl or isobutyl.

A lower alkoxy (or alkyloxy) group preferably contains 1–4 carbon atoms, and represents for example ethoxy, propoxy, isopropoxy, or most advantageously methoxy.

Halogen (or halo) preferably represents chloro or fluoro but may also be bromo or iodo.

Aryl represents carbocyclic or heterocyclic aryl.

Aroyl is carbocyclic or heterocyclic arylcarbonyl.

Carbocyclic aryl represents monocyclic or bicyclic aryl, for example phenyl or phenyl mono-, di- or tri-substituted by one, two or three radicals selected from lower alkyl, lower alkoxy, hydroxy, halogen, cyano, trifluoromethyl, lower alkylenedioxy and oxy-$C_2$–$C_3$-alkylene; or 1- or 2-naphthyl. Lower alkylenedioxy is a divalent substituent attached to two adjacent carbon atoms of phenyl, e.g. methylenedioxy or ethylenedioxy. Oxy-$C_2$–$C_3$-alkylene is also a divalent substituent attached to two adjacent carbon atoms of phenyl, e.g. oxyethylene or oxypropylene. An example for oxy-$C_2$–$C_3$-alkylene-phenyl is 2,3-dihydrobenzofuran-5-yl.

Preferred as carbocyclic aryl is phenyl or phenyl monosubstituted by lower alkoxy, halogen, lower alkyl or trifluoromethyl, especially phenyl or phenyl monosubstituted by lower alkoxy, halogen or trifluoromethyl, and in particular phenyl.

Heterocyclic aryl represents monocyclic or bicyclic heteroaryl, for example pyridyl, indolyl, benzoxazinyl, quinolinyl, isoquinolinyl, benzothienyl, benzofuranyl, benzopyranyl, benzotriazolyl, benzoxazolyl, furanyl, pyrrolyl, thiazolyl, oxazolyl, isoxazolyl, triazolyl, tetrazolyl, pyrazolyl, imidazolyl, thienyl, or any said radical substituted, especially mono- or di-substituted, by e.g. lower alkyl or halogen. Pyridyl represents 2-, 3- or 4-pyridyl, advantageously 3- or 4-pyridyl. Thienyl represents 2- or 3-thienyl, advantageously 2-thienyl. Quinolinyl represents preferably 2-, 3- or 4-quinolinyl, advantageously 2-quinolinyl. Isoquinolinyl represents preferably 1-, 3- or 4-isoquinolinyl. Benzopyranyl, benzothiopyranyl represent preferably 3-benzopyranyl or 3-benzothiopyranyl, respectively. Thiazolyl represents preferably 2- or 4-thiazolyl, advantageously 4-thiazolyl. Triazolyl is preferably 1-, 2- or 5-(1,2,4-triazolyl). Tetrazolyl is preferably 5-tetrazolyl. Imidazolyl is preferably 4-imidazolyl.

Preferably, heterocyclic aryl is pyridyl, quinolinyl, pyrrolyl, thiazolyl, isoxazolyl, triazolyl, tetrazolyl, pyrazolyl, imidazolyl, thienyl, or any said radical substituted, especially mono- or di-substituted, by lower alkyl or halogen; and in particular pyridyl.

Biaryl is preferably carbocyclic biaryl, e.g. biphenyl, namely 2-, 3- or 4-biphenyl, advantageously 4-biphenyl, each optionally substituted by e.g. lower alkyl, lower alkoxy, halogen, trifluoromethyl or cyano.

Cycloalkyl represents a saturated cyclic hydrocarbon optionally substituted by lower alkyl which contains 3 to 10 ring carbons and is advantageously cyclopentyl, cyclohexyl, cycloheptyl or cyclooctyl optionally substituted by lower alkyl.

Carbocyclic aryl-lower alkyl represents preferably straight chain or branched aryl-$C_1$–$C_4$-alkyl in which carbocyclic aryl has meaning as defined above, e.g. benzyl or phenyl-(ethyl, propyl or butyl), each unsubstituted or substituted on phenyl ring as defined under carbocyclic aryl above, advantageously optionally substituted benzyl.

Heterocyclic aryl-lower alkyl represents preferably straight chain or branched heterocyclic aryl-$C_1$–$C_4$-alkyl in which heterocyclic aryl has meaning as defined above, e.g. 2-, 3- or 4-pyridylmethyl or (2-, 3- or 4-pyridyl)-(ethyl, propyl or butyl); or 2- or 3-thienylmethyl or (2- or 3-thienyl)-(ethyl, propyl or butyl); 2-, 3- or 4-quinolinylmethyl or (2-, 3- or 4-quinolinyl)-(ethyl, propyl or butyl); or 2- or 4-thiazolylmethyl or (2- or 4-thiazolyl)-(ethyl, propyl or butyl).

Cycloalkyl-lower alkyl represents e.g. (cyclopentyl- or cyclohexyl)-(methyl or ethyl).

Acyl is derived from an organic carboxylic acid, carbonic acid or carbamic acid.

Acyl represents e.g. lower alkanoyl, carbocyclic aryl-lower alkanoyl, lower alkoxycarbonyl, aroyl, di-lower alkylaminocarbonyl or di-lower alkylamino-lower alkanoyl. Preferably, acyl is lower alkanoyl.

Lower alkanoyl represents e.g. $C_1$–$C_7$-alkanoyl including formyl, and is preferably $C_2$–$C_4$-alkanoyl such as acetyl or propionyl.

Aroyl represents e.g. benzoyl or benzoyl mono- or di-substituted by one or two radicals selected from lower alkyl, lower alkoxy, halogen, cyano and trifluoromethyl; or 1- or 2-naphthoyl; and also e.g. pyridylcarbonyl.

Lower alkoxycarbonyl represents preferably $C_1$–$C_4$-alkoxycarbonyl, e.g. ethoxycarbonyl.

Lower alkylene represents either straight chain or branched alkylene of 1 to 7 carbon atoms and represents preferably straight chain alkylene of 1 to 4 carbon atoms, e.g. a methylene, ethylene, propylene or butylene chain, or said methylene, ethylene, propylene or butylene chain mono-substituted by $C_1$–$C_3$-alkyl (advantageously methyl) or disubstituted on the same or different carbon atoms by $C_1$–$C_3$-alkyl (advantageously methyl), the total number of carbon atoms being up to and including 7.

Lower alkylenedioxy is preferably ethylenedioxy or methylenedioxy.

Esterified carboxyl is for example lower alkoxycarbonyl or benzyloxycarbonyl.

Amidated carboxyl is for example aminocarbonyl, mono- or di-lower alkylaminocarbonyl.

A particular embodiment of the invention consists of the compounds of formula I wherein R represents acyl derived from a carbonic acid, namely compounds of formula II

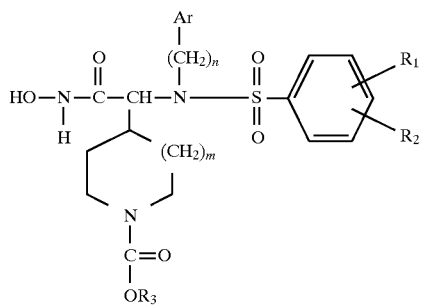

wherein Ar, $R_1$, $R_2$, m and n have meaning as defined above; $R_3$ is lower alkyl; or $R_3$ is lower alkyl which is substituted by carbocyclic or heterocyclic aryl, biaryl, adamantyl, cycloalkyl, bicycloalkyl, alkoxy, phthalimido, 1,4-benzoxazin-3-onyl, benzoxazolonyl, amino, mono- or di-lower alkylamino, piperazino, N-lower alkylpiperazino, N-(carbocyclic or heterocyclic aryl-lower alkyl) piperazino, morpholino, thiomorpholino, piperidino, pyrrolidino, piperidinyl or N-lower alkylpiperidinyl, hexahydroazepino, hexahydroazepinyl or N-lower alkylhexahydroazepinyl, tetrahydroquinolinyl, tetrahydroisoquinolinyl or by lower alkoxy; pharmaceutically acceptable prodrug derivatives thereof; and pharmaceutically acceptable salts thereof.

Preferred are compounds of formula II wherein m is one.

Preferred are said compounds of formula II wherein Ar is pyridyl; m is one; n is one; $R_1$ and $R_2$ are hydrogen, lower alkoxy or halo; or $R_1$ and $R_2$ together on adjacent carbon atoms represent methylenedioxy; $R_3$ represents lower alkyl or lower alkyl substituted by quinolinyl, tetrahydroquinolinyl, pyridyl, carbocyclic aryl, indolyl or by phthalimido; pharmaceutically acceptable prodrug derivatives thereof; and pharmaceutically acceptable salts thereof.

Further preferred are said compounds of formula II wherein Ar is 3- or 4-pyridyl; $R_1$ is lower alkoxy at the para position and $R_2$ is hydrogen; $R_3$ represents lower alkyl or lower alkyl substituted by carbocyclic aryl; pharmaceutically acceptable prodrug derivatives and pharmaceutically acceptable salts thereof.

A further embodiment is represented by compounds of formula III

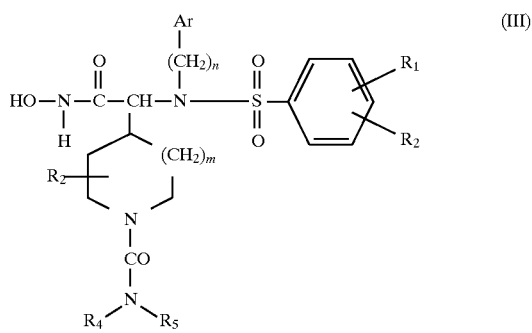

wherein Ar, $R_1$, $R_2$, m and n have meaning as defined hereinabove; $R_4$ and $R_5$ independently represent hydrogen, lower alkyl, aryl, aryl-lower alkyl or acyl derived from a carboxylic acid; or $R_4$ and $R_5$ combined represent lower alkylene or lower alkylene interrupted by O, S, NH or by N-lower alkyl; pharmaceutically acceptable prodrug derivatives thereof; and pharmaceutically acceptable salts thereof.

Preferred are said compounds of formula III wherein m is one.

Preferred in turn are said compounds of formula III wherein Ar is pyridyl; m is one; n is one; $R_1$ is lower alkoxy; and $R_2$ is hydrogen.

Further preferred are said compounds of formula III wherein Ar is 3- or 4-pyridyl; and $R_1$ is at the para-position.

A further embodiment of the invention represents compounds of formula I wherein R represents a sulfonyl group, namely compounds of formula IV

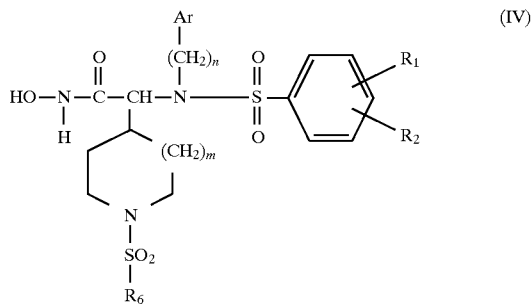

wherein Ar, $R_1$, $R_2$, m and n have meaning as defined above and $R_6$ represents lower alkyl, cycloalkyl, aryl-lower alkyl, aryl or di-(lower alkyl, aryl or aryl-lower alkyl)-amino.

Preferred are the compound of formula IV wherein m is one.

Preferred are said compound of formula IV wherein Ar is pyridyl; m is one; n is one; $R_1$ is lower alkoxy; and $R_2$ is hydrogen.

Further preferred are said compounds of formula IV wherein Ar is 3 or 4-pyridyl; and $R_1$ is at the para position.

A further embodiment of the invention relates to compounds of formula I wherein R represents acyl derived from a carboxylic acid, namely compounds of formula V

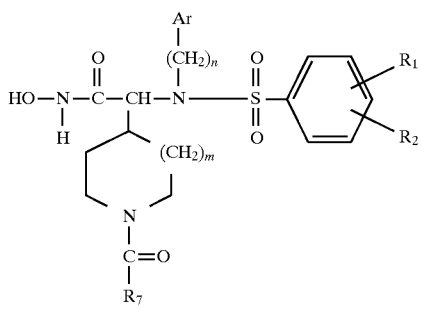

wherein Ar, $R_1$, $R_2$, m and n have meaning as defined hereinabove and $R_7$ represents lower alkyl, aryl-lower alkyl, carbocyclic or heterocyclic aryl, cycloalkyl, cycloalkyl-lower alkyl, adamantyl, bicycloalkyl, or biaryl.

Preferred are compounds of formula V wherein m is one.

Preferred are said compounds of formula V wherein Ar is pyridyl; m is one; n is one; $R_1$ and $R_2$ are hydrogen, lower alkoxy or halo; or $R_1$ and $R_2$ together on adjacent carbon atoms represent methylenedioxy; and $R_7$ represents lower alkyl or aryl-lower alkyl.

Further preferred are said compounds of formula V wherein Ar is pyridyl; m is one; n is one; $R_1$ is lower alkoxy; $R_2$ is hydrogen; and $R_7$ represents lower alkyl or aryl-lower alkyl.

Further preferred are said compounds wherein Ar is 3- or 4- pyridyl; and $R_1$ is para-lower alkoxy; $R_2$ is hydrogen; and $R_7$ is lower alkyl or aryl-lower alkyl.

The compounds of the invention exhibit valuable pharmacological properties in mammals including man, particularly as inhibitors of TNF-α activity and as inhibitors of matrix-degrading metalloproteinase enzymes.

The compounds are therefore particularly useful for the treatment of e.g. inflammatory conditions such as rheumatoid arthritis, of tumors and the other TNF-α-dependent or metalloproteinase-dependent conditions, e.g. those described hereinabove.

Beneficial effects are evaluated in pharmacological tests generally known in the art, and as illustrated herein.

The above-cited properties are demonstrable in in vitro and in vivo tests, using advantageously mammals, e.g. rats, guinea pigs, dogs, rabbits, or isolated organs and tissues, as well as mammalian enzyme preparations. Said compounds can be applied in vitro in the form of solutions, e.g. preferably aqueous solutions, and in vivo either enterally or parenterally, advantageously orally, e.g. as a suspension or in aqueous solution. The dosage in vitro may range between about $10^{-5}$ molar and $10^{-10}$ molar concentrations. The dosage in vivo may range, depending on the route of administration, between about 0.1 and 100 mg/kg.

The inhibition of the production of secretion of TNF-alpha (by inhibition of TNF-α convertase) can be determined e.g. as described in Nature 370, 555, 558 (1994).

The effect on the production of soluble TNF-alpha by LPS-stimulated THP-1 cells can be determined as follows:

Tissue culture medium used is RPM 1640 (Gibco cat #11874-036) containing 10% fetal calf serum, 1% penicillin and streptomycin. THP-1 cells (ATCC #202-TIB) at 1×10+5 cells/well are added to 100 μl medium or test compound. Cells are pre-incubated with compound for 30 minutes in a 37° C. humidified chamber with 5% $CO_2$ and then stimulated with 100 ng/ml of LPS (Sigma cat #L-4391) for 4 hours. Plates are then centrigued and 100 μl of conditioned medium for TNF analysis is harvested. The amount of TNF-alpha in control and test cultures is determined by ELISA using recombinant TNF-alpha for the standard curve, using TNF ELISA plates (Genzyme) for TNF analysis. Absorbance readings and data calculations are performed on a Molecular Devices plate reader. Results are expressed in $IC_{50}$'s of test compound.

Illustrative of the invention the compound of example 1(a) exhibits an $IC_{50}$ of about 0.7 μM in the above assay.

The effect on the plasma concentration of TNF-alpha in the mouse following intravenous injection of endotoxin can be determined as follows:

Female Balb-CbyJ mice are dosed by gavage with test compound in 0.1 ml cornstarch vehicle/10 grams body weight. One to four hours after administration of test compound, 0.1 mg/kg Lipopolysaccharide from E. coli 0127:B8 (Difco #3880-25-0) in saline is injected i.v. One hour after i.v. injection of LPS, blood is collected for determination of plasma TNF-alpha using mouse TNF-alpha ELISA kit (Gernzyme). Eight mice are used per treatment group. Results are expressed as % inhibition of mean TNF-alpha concentration in control mice.

The effect on the synovial fluid concentration of TNF-alpha in an inflamed rat knee can be determined as follows:

Female Lewis rats are dosed by gavage with test compound in 0.1 ml cornstarch vehicle. One to four hours after administration of test compound 0.1 mg Lipopolysaccharide from E. coli 0127. B8 (Diffco #3880-25-0) is injected into both knees. Two hours after intra-articular LPS injection, knees are lavaged with 0.1 ml saline and 2 lavages from same rat are pooled. TNF-alpha is measured using mouse TNF-alpha ELISA kit (Genzyme) which crossreacts with rat TNF-alpha. Results are expressed as % inhibition of mean TNF-alpha concentration in synovial fluid from saline-injected knees.

Antiinflammatory activity can be determined in standard inflammation and arthritic animal models well-known in the art. e.g. the adjuvant arthritis model in rats and the collagen II induced arthritis model in mice (Mediators of Inflam. 1, 273–279 (1992).

One test to determine the inhibition of stromelysin activity is based on its hydrolysis of Substance P using a modified procedure of Harrison et al (Harrison, R. A., Teahan J., and Stein R., A semicontinuous, high performance chromatography based assay for stromelysin, Anal. Biochem. 180, 110–113 (1989)). In this assay, Substance P is hydrolyzed by recombinant human stromelysin to generate a fragment, Substance P 7-11, which can be quantitated by HPLC. In a typical assay, a 10 mM stock solution of a compound to be tested is diluted in the assay buffer to 50 μM, mixed 1:1 with 8 μg recombinant human stromelysin (mol. wt. 45–47 kDa, 2 Units; where 1 Unit produces 20 moles of Substance P 7-11 in 30 minutes) and incubated along with 0.5 mM Substance P in a fmal volume of 0.125 ml for 30 minutes at 37° C. The reaction is stopped by adding 10 mM EDTA and Substance P 7-11 is quantified on RP-8 HPLC. The $IC_{50}$ for inhibition of stromelysin activity and Ki are calculated from control reaction without the inhibitor.

Illustrative of the invention, the compound of example 1(a) exhibits an $IC_{50}$ of about 15 nM in the assay.

Stromelysin activity can also be determined using human aggrecan as a substrate. This assay allows the confirmation in-vitro that a compound can inhibit the action of stromelysin on its highly negatively-charged natural substrate, aggrecan (large aggregating proteoglycan). Within the cartilage, proteoglycan exists as an aggregate bound to hyaluronate. Human proteoglycan aggregated to hyaluronate is used as an enzyme substrate. The assay is set up in 96-well microtiter plates allowing rapid evaluation of compounds. The assay has three major steps:

1) Plates are coated with hyaluronate (human umbilical chord, 400 ug/ml), blocked with BSA (5 mg/ml), and then proteoglycan (human articular cartilage D1—chondroitinase ABC digested, 2 mg/ml) is bound to the hyaluronate. Plates are washed between each step.

2) Buffers+inhibitor (1 to 5,000 nM)+recombinant human stromelysin (1–3 Units/well) are added to wells. The plates are sealed with tape and incubated overnight at 37° C. The plates are then washed.

3) A primary (3B3) antibody (mouse IgM, 1:10,000) is used to detect remaining fragments. A secondary antibody, peroxididase-linked anti-IgM, is bound to the primary antibody. OPD is then added as a substrate for the peroxidase and the reaction is stopped with sulfuric acid. The $IC_{50}$ for inhibition of stromelysin activity is graphically derived and $K_i$ is calculated.

Collagenase activity is determined as follows: ninety six-well, flat-bottom microtiter plates are first coated with bovine type I collagen (35 ug/well) over a two-day period at 30° C. using a humidified and then dry atmosphere; plates are rinsed, air dried for 3–4 hours, sealed with Saran wrap and stored in a refrigerator. Human recombinant fibroblast collagenase and a test compound (or buffer) are added to wells (total volume=0.1 ml) and plates are incubated for 2 hours at 35° C. under humidified conditions; the amount of collagenase used per well is that causing approximately 80% of maximal digestion of collagen. The incubation media are removed from the wells, which are then rinsed with buffer, followed by water. Coomasie blue stain is added to the wells for 25 minutes, removed, and wells are again rinsed with water. Sodium dodecyl sulfate (20% in 50% dimethylformamide in water) is added to solubilize the remaining stained collagen and the optical density at 570 nM wave length is measured. The decrease in optical density due to collagenase (from that of collagen without enzyme) is compared to the decrease in optical density due to the enzyme in the presence of test compound, and percent inhibition of enzyme activity is calculated. $IC_{50}$'s are determined from a range of concentrations of inhibitors (4–5 concentrations, each tested in triplicate), and $K_i$ values are calculated.

Illustrative of the invention, the compounds of examples 1(a) exhibit an $IC_{50}$ of about 109 nM in this assay.

The effect of compounds of the invention in-vivo can be determined in rabbits. Typically, four rabbits are dosed orally with a compound up to four hours before being injected intra-articularly in both knees (N=8) with 40 Units of recombinant human stromelysin dissolved in 20 mM Tris, 10 mM $CaCl_2$, and 0.15M NaCl at pH 7.5. Two hours later the rabbits are sacrificed, synovial lavage is collected, and keratan sulfate (KS) and sulfated glycosaminoglycan (S-GAG) fragments released into the joint are quantitated. Keratan sulfate is measured by an inhibition ELISA using the method of Thonar (Thonar, E. J.-M. A., Lenz, M. E., Klinsworth, G. K., Caterson, B., Pachman, L. M., Glickman, P., Katz, R., Huff, J., Keuttner, K. E. Quantitation of keratan sulfate in blood as a marker of cartilage catabolism, Arthr. Rheum. 28, 1367–1376 (1985)). Sulfated glycosaminoglycans are measured by first digesting the synovial lavage with streptomyces hyaluronidase and then measuring DMB dye binding using the method of Goldberg (Goldberg, R. L. and Kolibas, L. An improved method for determining proteoglycan synthesized by chondrocytes in culture. Connect. Tiss. Res. 24, 265–275 (1990)). For an i.v. study, a compound is solubilized in 1 ml of PEG-400, and for a p.o. study, a compound is administered in 5 ml of fortified corn starch per kilogram of body weight.

The effect in protecting against cartilage degradation in arthritic disorders can be determined e.g. in a surgical model of osteoarthritis described in Arthritis and Rheumatism, Vol. 26, 875–886 (1983).

The effect on ulcerations, e.g. ocular ulcerations, can be determined in the rabbit by measuring the reduction of corneal ulceration following an alkali burn to the cornea.

Macrophage metalloelastase (MME) inhibitory activity can be determined by measuring the inhibition of the degradation of [$^3$H]-elastin by truncated recombinant mouse macrophage metalloelastase as follows:

About 2 ng of recombinant truncated mouse macrophage metalloelastase (FASEB Journal Vol. 8, A151, 1994), purified by Q-Sepharose column chromatography is incubated with test compounds at the desired concentrations in the presence of 5 nM $CaCl_2$, 400 nM NaCl, [$^3$H]elastin (60,000 cpm/tube), and 20 mM Tris, pH 8.0, at 37° C. overnight. The samples are spun in a microfuge centrifuge at 12,000 rpm for 15 minutes. An aliquot of the supernatant is counted in a scintillation counter to quantitate degraded [$^3$H]elastin. $IC_{50}$'s are determined from a range of concentrations of the test compounds and the percent inhibition of enzyme activity obtained.

The effect of the compounds of the invention for the treatment of emphysema can be determined in animal models described in American Review of Respiratory Disease 117, 1109 (1978).

The antitumor effect of the compounds of the invention can be determined e.g. by measuring the growth of human tumors implanted subcutaneously in Balb/c nude treated mice according to methodology well-known in the art in comparison to placebo treated mice. Illustrative tumors are e.g. estrogen dependent human breast carcinoma BT20 and MCF7, human bladder carcinoma T24, human colon carcinoma Colo 205, human lung adenocarcinoma A549 and human ovarian carcinoma NIH-OVCAR3.

The effect on tumor angiogenesis can be determined e.g. in rats implanted with Walker 256 carcinoma in pellets to stimulate angiogenesis from vessels of the limbus, as described by Galardy et al, Cancer Res. 54, 4715 (1994).

The effect of the compounds of the invention on atherosclerotic conditions can be evaluated using atherosclerotic plaques from cholesterol-fed rabbits which contain activated matrix metalloproteinases as described by Sukhova et al, Circulation 90, I 404 (1994). The inhibitory effect on matrix metalloproteinase enzyme activity in rabbit atherosclerotic plaques can be determined by in situ zymography, as described by Galis et al, J. Clin. Invest. 94, 2493 (1994), and is indicative of plaque stabilization. The effect on restenosis and vascular remodeling can be evaluated in the rat ballooned carotid artery model.

The effect on vascular aneurysms, e.g. the inhibition of aneurysm formation, can be determined in experimental models such as Apo-E transgenic mice and/or LDL receptor knockout mice.

The effect on demyelinating disorders of the nervous system, such as multiple sclerosis, can be evaluated by measuring the reversal of experimental antioimmune encephalo-myelitis in mice, e.g. as described by Gijbels et al, J. Clin. Invest. 94, 2177 (1994).

As inhibitors of TNF-alpha convertase and matrix metalloproteinases the compounds of the invention are particularly useful in mammals as antiinflammatory agents for the treatment of e.g. osteoarthritis, rheumatoid arthritis, as antitumor agents for the treatment and prevention of tumor growth, tumor metastasis, tumor invasion or progression, and as antiatherosclerotic agents for the treatment and prevention of the rupture of atherosclerotic plaques.

The compounds of formula I can be prepared e.g. by condensing a carboxylic acid of formula VI

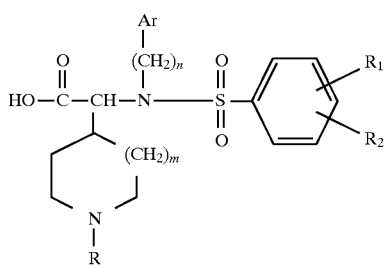

or a reactive functional derivative thereof, wherein Ar, m, n, R, $R_1$ and $R_2$ having meaning as defined hereinabove, with hydroxylamine of formula VII.

$$NH_2-OH \qquad (VII)$$

optionally in protected form, or a salt thereof;

and, if necessary, temporarily protecting any interfering reactive group(s), and then liberating the resulting compound of the invention; and, if required or desired, converting a resulting compound of the invention into another compound of the invention, and/or, if desired, converting a resulting free compound into a salt or a resulting salt into a free compound or into another salt; and/or separating a mixture of isomers or racemates obtained into the single isomers or racemates; and/or, if desired, resolving a racemate into the optical antipodes.

In starting compounds and intermediates which are converted to the compounds of the invention in a manner described herein, functional groups present, such as amino, carboxyl and hydroxy groups, are optionally protected by conventional protecting groups that are common in preparative organic chemistry. Protected amino, carboxyl and hydroxy groups are those that can be converted under mild conditions into free amino and hydroxy groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxy group, amino group, etc.), the structure and stability of the molecule of which the substituent is a part and the reaction conditions.

Well-known protecting groups that meet these conditions and their introduction and removal are described, for example, in J. F. W. McOmie, "Protective Groups in Organic Chemistry", Plenum Press, London, New York, 1973, T. W. Greene, "Protective Groups in Organic Synthesis", Wiley, New York, 1991.

In the processes cited herein, reactive functional derivatives of carboxylic acids represent, for example, anhydrides especially mixed anhydrides, acid halides, acid azides, lower alkyl esters and activated esters thereof. Mixed anhydrides are preferably such from pivalic acid, or a lower alkyl (ethyl, isobutyl) hemiester of carbonic acid; acid halides are for example chlorides or bromides; activated esters for example succinimido, phthalimido or 4-nitrophenyl esters; lower alkyl esters are for example the methyl or ethyl esters.

Also, a reactive esterified derivative of an alcohol in any of the reactions cited herein represents said alcohol esterified by a strong acid, especially a strong inorganic acid, such as a hydrohalic acid, especially hydrochloric, hydrobromic or hydroiodic acid, or sulphuric acid, or by a strong organic acid, especially a strong organic sulfonic acid, such as an aliphatic or aromatic sulfonic acid, for example methanesulfonic acid, 4-methylbenzenesulfonic acid or 4-bromobenzenesulfonic acid. A said reactive esterified derivative is especially halogen, for example chloro, bromo or iodo, or aliphatically or aromatically substituted sulfonyloxy, for example methanesulfonyloxy, 4-methylbenzenesulfonyloxy (tosyloxy) or trifluoromethanesulfonyloxy.

The above process for the synthesis of compounds of the invention can be carried out according to methodology generally known in the art for the preparation of hydroxamic acids and derivatives thereof.

The synthesis according to the above process (involving the condensation of a free carboxylic acid of formula VI with an optionally hydroxy protected hydroxylamine derivative of formula VII can be carried out in the presence of a condensing agent, e.g. 1,1'-carbonyldiimidazole, or N-(dimethylaminopropyl)-N'-ethylcarbodiimide, or dicyclohexylcarbodiimide, with or without 1-hydroxybenzotriazole or 1-hydroxy-7-azabenzotriazole, in an inert polar solvent such as dimethylformamide or dichloromethane, preferably at room temperature.

The synthesis involving the condensation of a reactive functional derivative of an acid of formula VI as defined above, e.g. an acid chloride or mixed anhydride with optionally hydroxy protected hydroxylamine, or a salt thereof, in presence of a base such as triethylamine can be carried out, at a temperature ranging preferably from about −78° C. to +75° C., in an inert organic solvent such as dichloromethane or toluene.

Protected forms of hydroxylamine (of formula VII) in the above process are those wherein the hydroxy group is protected for example as a t-butyl ether, a benzyl ether, a triphenylmethyl (trityl)ether, a tetrahydropyranyl ether, or as a trimethylsilyl derivative. Removal of said protecting groups is carried out according to methods well known in the art, e.g. hydrogenolysis or acid hydrolysis. Hydroxylamine is preferably generated in situ from a hydroxylamine salt, such as hydroxylamine hydrochloride.

The starting carboxylic acids of formula VI can be prepared as follows:

An amino acid or ester of formula VIII

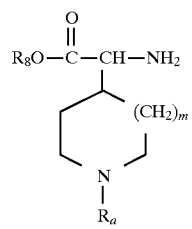

wherein m is 0 or 1, $R_8$ is hydrogen or a carboxyl protecting group, e.g. lower alkyl or benzyl, and Ra is an amino protecting group, e.g. t-BOC, is treated with a reactive functional derivative of the appropriate sulfonic acid of the formula IX

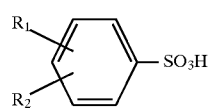

wherein $R_1$ and $R_2$ have meaning as defined hereinabove, e.g. with the corresponding sulfonyl chloride, in the presence of a suitable base, such as triethylamine or dicyclohexylamine, using a polar solvent such as tetrahydrofuran, dioxane or acetonitrile to obtain a compound of the formula X

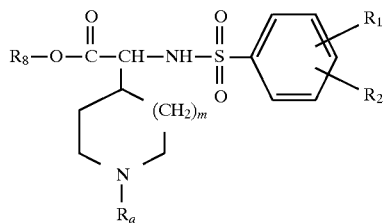

wherein R, $R_1$, $R_2$, m, n, $R_a$ have meaning as defined above and R8 is hydrogen or a carboxyl protecting group, e.g. lower alkyl or benzyl.

The starting materials of formula VIII, IX and XI are either known in the art, or can be prepared by methods well-known in the art or as described herein.

Optically active D-aminoacids of formula VIII (the R-enantiomers) can be prepared according to methods known in the art, e.g. according to methods described in Coll. Czech. Comm. 49, 712–742 (1984), Angew. Chem. Int. Ed. (Engl.) 27, 1194 (1988), and Tetrahedron Letters, 33, 1189 (1992).

For example, (R)-N-t-Boc-4-piperidinylglycine can be prepared by enantioselective synthesis using optically active (R)-4-benzyl-2-oxazolidinone as generally described by Evans et al, Tetrahedron Letters 33, 1189–1192 (1992).

N-t-Boc-4-piperidinylacetic acid is converted to the mixed anhydride (e.g. with pivaloyl chloride/triethylamine) which is condensed with (R)(+)-4-benzyl-2-oxazolidinone to obtain 3-[2-t-Boc-4-piperidinyl-1-oxoethyl]-4-(R)-benzyl-2-oxazolidinone. Treatment with potassium bis-(trimethylsilylamide) followed by 2,4,6-triisopropylbenzenesulfonyl azide (trisyl azide) yields the diastereomeric azide of the formula

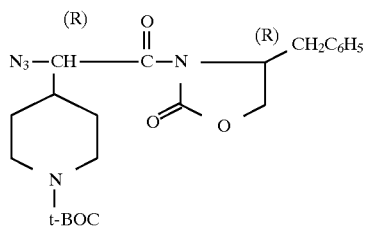

which is converted by treatment with hydrogen peroxide/LiOH to 2(R)-azido-2-(N-t-Boc-4-piperidinyl)-acetic acid which is in turn catalitically hydrogenated to obtain (R)-N-t-Boc-4-piperidinyl)-glycine, the compound of formula VIII in which m is one, $R_8$ is hydrogen and $R_a$ is t-Boc.

Treatment of an intermediate of formula X wherein $R_8$ is a carboxyl protecting group, e.g. benzyl, with a reactive esterified derivative (such as the halide, e.g. the chloride, bromide or iodide derivative) of the alcohol of the formula XI $$Ar-(CH_2)_nOH \qquad (XI)$$

wherein Ar and n have meaning as defined herein, in the presence of an appropriate base, such as cesium carbonate or dicyclohexylamine, in a polar solvent, such as dimethylformamide yields an intermediate of formula XII

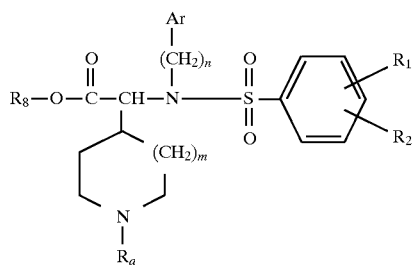

wherein Ar, Ra, $R_1$, $R_2$, $R_8$, m and n have meaning as defined hereinabove.

Selective removal of the aminoprotecting group $R_a$, e.g. with anhydrous hydrogen chloride if $R_a$ is t-Boc, yields a compound of formula XIII

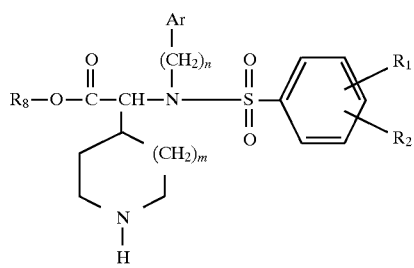

wherein Ar, $R_a$, $R_1$, $R_2$, m and n have meaning as previously described, and $R_8$ is a carboxyl protecting group (e.g. benzyl). N-substitution of a resulting ester intermediate of formula XIII with a reactive derivative corresponding to the R substituent in formula I leads to the ester, e.g. the benzyl ester of a compound of formula VI. Such can be converted to the acid of formula VI, by standard methods, e.g. by catalytic hydrogenation if $R_8$ is benzyl.

N-substitution of a compound of formula XIII can be carried out as follows.

(a) For intermediates of formula VI leading to compounds of formula I wherein R is acyl derived from a carbonic acid (the urethanes of formula II) by
 (i) treating a compound of formula XIII with a compound of the formula XIV

wherein $R_3$ has meaning as defined hereinabove and X is a leaving group, such as halo, preferably chloro, in the presence of a base such as triethylamine; or by
 (ii) reacting a compound of formula XIII with a reactive derivative of carbonic acid, e.g. phosgene or di(2-pyridyl)carbonate, and an alcohol of formula XV $$R_3-OH \qquad (XV)$$

wherein $R_3$ has meaning as previously described, in an inert solvent and in the presence of a base such as triethylamine;
(b) For intermediates of formula VI leading to compounds of formula I wherein R is acyl derived from a carboxylic acid (the amides of formula V), by
 (i) treating a compound of formula XIII with a reactive functional derivative of a carboxylic acid of the formula XVI $$R_7-COOH \qquad (XVI)$$

wherein R₇ has meaning as previously described, e.g. with an acid anhydride or acid chloride, in the presence of a base such as triethylamine, or (ii) reacting a compound of formula XIII with a carboxylic acid of formula XVI in a presence of a condensing agent, e.g. a carbodiimide such as 1-ethyl-3-(3-dimethylaminopropyl)carbodiimide with e.g. 1-hydroxy-7-aza-benzotriazole, and a base such as N-methylmorpholine;

(c) for intermediates of formula VI leading to compounds of formula I wherein R is acyl derived from a carbamic acid (the ureas of formula III) by (i) treating a compound of formula XIII with an isocyanate compound of the formula XVII

  (XVII)

to obtain a compound of formula III wherein R₄ has meaning other than hydrogen as defined herein above and R₅ is hydrogen, and if desired further alkylating or acylating the obtained intermediate or (ii) reacting a compound of formula XIII with a reactive derivative of carbamic acid, e.g. phosgene, and an amine of the formula XVIII

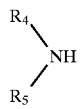  (XVIII)

wherein R₄ and R₅ have meaning as defined hereinabove in an inert solvent and in the presence of a base, such as triethylamine;

(d) for intermediates of formula VI leading to compounds of formula I wherein R is substituted sulfonyl (the compounds of formula IV) by (i) treating a compound of formula XIII with a reactive functional derivative of a sulfonic acid of the formula XIX

  (XIX)

wherein R₆ has meaning as previously defined, e.g. with a sulfonic acid halide (e.g. an arylsulfonyl chloride such as tosyl chloride or a dialkylsulfamoyl chloride such as dimethylsulfamoyl chloride) in the presence of a base, such as triethylamine.

(e) for intermediates of formula VI leading to compounds of formula I wherein R is e.g. aryl-lower alkyl by treating a compound of formula XIII with a reactive esterified derivative of the corresponding alcohol, e.g. the bromide, or iodide thereof, in the presence of a base, e.g. potassium carbonate; and converting any of the so obtained ester intermediates to the corresponding carboxylic acids of formula VI using either hydrogenolysis or standard mild methods of ester hydrolysis, preferably under acidic conditions, the method depending on the nature of the esterifying group.

The above-mentioned reactions are carried out according to standard methods, in the presence or absence of diluent, preferably such as are inert to the reagents and as solvents thereof, of catalysts, condensing or said other agents respectively and/or inert atmospheres, at low temperatures, room temperature or elevated temperatures (preferably at or near the boiling point of the solvents used), and at atmospheric or super-atmospheric pressure. The preferred solvents, catalysts and reaction conditions are set forth in the appended illustrative examples.

The invention further includes any variant of the present processes, in which an intermediate product obtainable at any stage thereof is used as starting material and the remaining steps are carried out, or the process is discontinued at any stage thereof, or in which the starting materials are formed in situ under the reaction conditions, or in which the reaction components are used in the form of their salts or optically pure antipodes.

Compounds of the invention and intermediates can also be converted into each other according to methods generally known per se.

The invention also relates to any novel starting materials and processes for their manufacture.

Depending on the choice of starting materials and methods, the new compounds may be in the form of one of the possible isomers or mixtures thereof, for example, as substantially pure geometric (cis or trans) isomers, optical isomers (antipodes), racemates, or mixtures thereof. The aforesaid possible isomers or mixtures thereof are within the purview of this invention.

Any resulting mixtures of isomers can be separated on the basis of the physico-chemical differences of the constituents, into the pure geometric or optical isomers, diastereoisomers, racemates, for example by chromatography and/or fractional crystallization.

Any resulting racemates of final products or intermediates can be resolved into the optical antipodes by known methods, e.g. by separation of the diastereoisomeric salts thereof, obtained with an optically active acid or base, and liberating the optically active acidic or basic compound. The hydroxamic acids or carboxylic acid intermediates can thus be resolved into their optical antipodes e.g. by fractional crystallization of d- or l-(alpha-methylbenzylamine, cinchonidine, cinchonine, quinine, quinidine, ephedrine, dehydroabietylamine, brucine or strychnine)-salts; or by enantioselective chromatography.

Finally, acidic compounds of the invention are either obtained in the free form, or as a salt thereof.

Acidic compounds of the invention may be converted into salts with pharmaceutically acceptable bases, e.g. an aqueous alkali metal hydroxide, advantageously in the presence of an ethereal or alcoholic solvent, such as a lower alkanol. From the solutions of the latter, the salts may be precipitated with ethers, e.g. diethyl ether. Resulting salts may be converted into the free compounds by treatment with acids. These or other salts can also be used for purification of the compounds obtained.

Compounds of the invention having basic groups can be converted into acid addition salts, especially pharmaceutically acceptable salts. These are formed, for example, with inorganic acids, such as mineral acids, for example sulfuric acid, a phosphoric or hydrohalic acid, or with organic carboxylic acids, such as ($C_1$–$C_4$)-alkanecarboxylic acids which, for example, are unsubstituted or substituted by halogen, for example acetic acid, such as saturated or unsaturated dicarboxylic acids, for example oxalic, succinic, maleic or fumaric acid, such as hydroxycarboxylic acids, for example glycolic, lactic, malic, tartaric or citric acid, such as amino acids, for example aspartic or glutamic acid, or with organic sulfonic acids, such as ($C_1$–$C_4$)-alkane- or arylsulfonic acids which are unsubstituted or substituted, for example, by halogen, for example methanesulfonic acid. Preferred are salts formed with hydrochloric acid, methanesulfonic acid and maleic acid.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The pharmaceutical compositions according to the invention are those suitable for enteral, such as oral or rectal, transdermal and parenteral administration to mammals, including man, to inhibit TNF-alpha converting enzyme and matrix-degrading metalloproteinases, and for the treatment of disorders responsive thereto, comprising an effective amount of a pharmacologically active compound of the invention, alone or in combination, with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salt and/or polyethyleneglycol; for tablets also c) binders e.g. magnesium aluminum silicate, starch paste, gelatin, tragacanth, methylcellulose, sodium carboxymethylcellulose and or polyvinylpyrrolidone; if desired d) disintegrants, e.g. starches, agar, alginic acid or its sodium salt, or effervescent mixtures; and/or e) absorbants, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable formulations for topical application, e.g. to the skin and eyes, are preferably aqueous solutions, ointments, creams or gels well-known in the art.

The pharmaceutical formulations contain an effective TNF-alpha convertase inhibiting amount and/or matrix-degrading metalloproteinase inhibiting amount of a compound of the invention as defined above, either alone or in combination with another therapeutic agent, e.g. an anti-inflammatory agent with cyclooxygenase inhibiting activity, or other antirheumatic agents such as methotrexate, each at an effective therapeutic dose as reported in the art. Such therapeutic agents are well-known in the art.

Examples of antiinflammatory agents with cyclooxygenase inhibiting activity are diclofenac, naproxen, ibuprofen, and the like.

In conjunction with another active ingredient, a compound of the invention may be administered either simultaneously, before or after the other active ingredient, either separately by the same or different route of administration or together in the same pharmaceutical formulation.

The dosage of active compound administered is dependent on the species of warm-blooded animal (mammal), the body weight, age and individual condition, and on the form of administration. A unit dosage for oral administration to a mammal of about 50 to 70 kg may contain between about 10 and 1000 mg, advantageously between about 25 and 250 mg of the active ingredient.

The present invention also relates to methods of using the compounds of the invention and their pharmaceutically acceptable salts, or pharmaceutical compositions thereof, in mammals for inhibiting TNF-alpha activity and/or inhibiting the matrix-degrading metalloproteinases, e.g. stromelysin, gelatinase, collagenase and macrophage metalloelastase, for inhibiting tissue matrix degradation, and for the treatment of TNF-alpha and matrix-degrading metalloproteinase dependent conditions as described herein, e.g. inflammation, rheumatoid arthritis, osteoarthritis, also tumors (tumor growth, metastasis, progression or invasion), pulmonary disorders, atherosclerosis and the like described herein. Tumors (carcinomas) include mammalian breast, lung, bladder, colon, prostate and ovarian cancer, and skin cancer, including melanoma and Kaposi's sarcoma.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg (=20–133 mbar). The structure of final products, intermediates and starting materials is confinmed by standard analytical methods, e.g. microanalysis and spectroscopic characteristics (e.g. MS, IR, NMR). Abbreviations used are those conventional in the art. The concentration for $[\alpha]_D$ determinations is expressed in mg/ml.

EXAMPLE 1

(a) N-(t-Butyloxy)-2-(R)-[(4-methoxybenzenesulfonyl) (4-picolyl)amino]-2-[(N-(2-(1-naphthyl)-ethoxycarbonyl))-4-piperidinyl]acetamide (3 g, 4.65 mmol) is dissolved in methylene chloride (100 ml) containing ethanol (0.27 ml, 4.6 mmol) and the reaction mixture is cooled to −10° C. Hydrochloric acid gas (from a lecture bottle) is bubbled trough the solution for 15 minutes. The flask is sealed, the reaction mixture is allowed to slowly warm to room temperature and stirred at room temperature for 6 days. The reaction mixture is concentrated in vacuo to provide N-hydroxy-2-(R)-[(4-methoxy-benzenesulfonyl) (4-picolyl) amino]-2- [(N-(2-(1-naphthyl)-ethoxycarbonyl))-4-piperidinyl]acetamide hydrochloride as a white solid, m.p. >137° C. (dec).

The starting material is prepared as follows:

To a solution of ethyl 4-pyridylacetate (49.97 g, 302 mmol) in 4N hydrochloric acid (200 ml) evacuated and purged with argon, is added platinum (IV) oxide (600 mg). The mixture is shaken in a Parr hydrogenation apparatus for 24 hours under a hydrogen pressure of 50 psi (=3.45 bar). The reaction mixture is filtered through celite which is rinsed with water (200 ml). The filtrate is basified to pH 9 by addition of sodium carbonate (43.9 g) and the resulting solution is stirred at 65° C. for 1 hour 40 minutes. The solution is concentrated in vacuo providing sodium 4-piperidylacetate as a white solid. To a solution of the crude product in water (400 ml) and dioxane (100 ml) at 0° C. is added a solution of di-tert-butyldicarbonate (66 g, 302 mmol) in dioxane (100 ml) in one portion. The reaction mixture is allowed to warm to room temperature and stirred for 50 hours with occasional addition of sodium carbonate to keep ca. pH 9. The reaction mixture is extracted with pentane, cooled to 0° C. and acidified to pH 4 by addition of 6N hydrochloric acid. The resulting cloudy mixture is extracted twice with diethyl ether, the combined organic layers are dried over sodium sulfate and the solvent is evaporated in vacuo to provide N-t-BOC-piperidine-4-acetic acid as a white solid.

To a solution of N-t-BOC-piperidine-4-acetic acid (48 g, 197.5 mmol) in tetrahydrofuran (700 ml) at −78° C. is added triethyl amine (35.8 ml, 257 mmol) followed by dropwise addition of pivaloyl chloride (26.7 ml, 217 mmol). The solution is stirred at −78° C. for 10 minutes, at 0° C. for 30 minutes and cooled back to −78° C. In a separate flask, R-(+)-4-benzyl-2-oxazolidinone (42 g, 237 mmol) is dissolved in tetrahydrofuran (450 ml) and cooled to −78° C. To this cold solution is added dropwise 2.5M n-butyl lithium in hexanes (95 ml, 237 mmol). The resulting solution is stirred at −78° C. for 10 minutes and added via cannula to the aforementioned solution over a period of 30 minutes. The resulting mixture is stirred at −78° C. for 30 minutes, allowed to warm to room temperature and filtered through celite. The filtrate is concentrated in vacuo at 35° C. The residue is dissolved in diethyl ether and washed with saturated aqueous sodium bicarbonate. The aqueous layer is extracted with diethyl ether and the combined organic layers are washed with water, with brine, and dried over magnesium sulfate. The solvent is evaporated in vacuo and the product is purified by silica gel chromatography (50% to 100% diethyl ether in hexane) to provide 3-[2-(N-t-BOC-4-piperidinyl)-1-oxoethyl]-4-(R)-(benzyl)-2-oxazilidinone.

To a solution of 3-[2-(N-t-BOC-4-piperidinyl)-1-oxoethyl]-4-(R)-(benzyl)-2-oxa zilidinone (63.4 g, 143 mmol) in tetrahydrofuran (1000 ml) cooled to −78° C. is added dropwise over 30 minutes a 0.5M solution of potassium bis-(trimethylsilylamide) in toluene (372 ml, 186 mmol). The resulting mixture is stirred at −78° C. for 20 minutes and a solution of 2,4,6- triisopropylbenzenesulfonyl azide (trisyl azide, 68.6 g, 221 mmol) in tetrahydrofuran (350 ml) cooled to −78° C. is cannulated over 30 minutes. After stirring at −78° C. for 20 minutes, acetic acid (30.5 ml, 532 mmol) is added and the reaction mixture is allowed to warm to room temperature. After dilution with diethyl ether (1500 ml), the organic layer is washed with saturated aqueous sodium bicarbonate, with brine and dried over sodium sulfate. The solvent is evaporated in vacuo and the residue is taken in diethyl ether. The resulting mixture is filtered, washed with water and brine, and concentrated in vacuo. The crude product is purified by silica gel chromatography (50% to 100% diethyl ether in hexane) to provide 3-[2-(R)-azido-2-(N-t-BOC-4-piperidinyl)-1-oxo-ethyl]-4-(R)-(benzyl)-2-oxazolidinone.

To a solution of 3-[2-(R)-azido-2-(N-t-BOC-4-piperidinyl)-1-oxo-ethyl]-4-(R)-(benzyl)-2-oxazol (63.4 g, 143 mmol) in tetrahydrofuran (1600 ml and wter (420 ml) cooled to 0° C. is added 30% aqueous hydrogen peroxide (58.4 ml, 572 mmol) followed by lithium hydroxide monohydrate (12 g, 286 mmol) and the resulting mixture is stirred at 0° C. for 1 hour and 20 minutes. Sodium sulfite (77.5 g, 615 mmol) is added and the reaction mixture is stirred at 0° C. for 10 minutes. The solvent is removed in vacuo at 30° C. and the residue is taken in water (600 ml). The mixture is extracted twice with methylene chloride, cooled to 0° C., acidified to pH 3–4 with 4N then 1N hydrochloric acid, and extracted twice with ethyl acetate. The combined organic layers are dried over sodium sulfate and concentrated in vacuo to give crude 2-(R)- azido-2-(N-t-BOC-4-piperidinyl)-acetic acid as a white solid.

To a solution of 2-(R)-azido-2-(N-t-BOC-4-piperidinyl)-acetic acid (20.9 g, 73.4 mmol) in ethanol (1400 ml) evacuated and purged with argon is added 10% palladium on carbon (2.1 g) and the reaction mixture is hydrogenated for 3 hours at room temperature under 1 atm hydrogen. The reaction mixture is filtered on celite and the solid residue is carefully washed with water 3 times. The combined filtrates are concentrated in vacuo to give crude (R)-(N-t-BOC-4-piperidinyl)-glycine which is used directly in the next reaction without further purification. The crude product from the above reaction is dissolved in water (350 ml) and dioxane (350 ml), and triethylamine (25.3 ml, 182 mmol) followed by 4-methoxybenzenesulfonyl chloride (13.15 g, 63.6 mmol) are added sequentially. The mixture is stirred at room temperature for 24 hours. The previous sequence is exactly repeated with 17.56 g of 2-(R)-azido-2-(N-t-BOC-4-piperidinyl)-acetic acid and the two reaction mixtures are combined before workup: the dioxane is removed in vacuo and the residue is taken in water and basified with saturated aqueous sodium bicarbonate. The resulting solution is extracted 4 times with diethyl ether, acidified to pH 2–3 with 6N and 1N hydrochloric acid and extracted with ethyl acetate 3 times. The combined organic layers are dried over sodium sulfate and concentrated in vacuo to give 2-(R)-[(4-methoxybenzenesulfonyl) amino]-2-(N-t-BOC-4-piperidinyl) acetic acid as a pale yellow solid.

To a solution of 2-(R)-[(4-methoxybenzenesulfonyl) amino]-2-(N-t-BOC-4-piperidinyl) acetic acid (39.25 g, 91.6 mmol) in dimethylformamide (500 ml) is added cesium carbonate (14.92 g, 45.8 mmol) followed by benzyl bromide (10.9 ml, 91.6 ml) and the reaction mixture is stirred at room temperature for 1 hour and 20 minutes. The reaction mixture is diluted with water and extracted with 1:1 diethyl ether/ ethyl acetate. The organic layer is washed twice with aqueous lithium chloride, dried over sodium sulfate and concentrated in vacuo. Purification by silica gel chromatography (40% to 100% diethyl ether in hexanes) provides benzyl 2-(R)-[(4-methoxybenzenesulfonyl)amino]-2-(N-t-BOC-4-piperidinyl)acetate as a white solid. To a solution of benzyl 2-(R)-[(4-methoxybenzenesulfonyl)amino]-2-(N-t-BOC-4-piperidinyl) acetate (36 g, 69.5 mmol) in dimethylformamide (500 ml) is added potassium carbonate powder (95.9 g, 690 mmol) followed by 4-picolyl chloride hydrochloride (11.63 g, 70.9 mmol) and the reaction mixture is stirred at room temperature for 24 hours. The reaction mixture is diluted with ethyl acetate (500 ml) and washed with water. The aqueous layer is extracted with ethyl acetate, the combined organic layers are washed with brine and aqueous lithium chloride, dried over sodium sulfate, and concentrated in vacuo. Purification by silica gel chromatography (65% to 100% ethyl acetate in hexanes) provides benzyl 2-(R)-[(4-methoxybenzenesulfonyl) (4-picolyl)amino]-2-(N-t-BOC-4-piperidinyl) acetate as a pale yellow amorphous solid.

Benzyl 2-(R)-[(4-methoxybenzenesulfonyl)(4-picolyl) amino]-2-(N-t-BOC-4-piperidinyl)acetate (35 g, 57.4 mmol) is dissolved in methylene chloride (900 ml) and cooled to 0° C. Hydrochloric acid gas is bubbled through the solution for 10 minutes and the flask is sealed. The reaction mixture is allowed to warm to room temperature and stirred for 1 hour. The reaction flask is carefully opened and nitrogen is bubbled trough the solution for 5 minutes. The solvent is removed in vacuo providing benzyl 2-(R)-[(4-methoxybenzenesulfonyl) (4-picolyl)amino]-2-(4-piperidinyl)acetate dihydrochloride as a white amorphous solid.

To a solution of 1-naphthaleneethanol (1.8 g, 10.45 mmol) in methylene chloride (40 ml) is added triethylamine (1.58 g, 15.7 mmol) and di(2-pyridyl) carbonate (2.26 g, 10.45 mmol, prepared according to Ghosh's procedure, Tetrahedron Lett. 1991, 32, 4251–4254), and the reaction mixture is stirred at room temperature for 18 hours. A solution of benzyl 2-(R)-[(4-methoxybenzenesulfonyl)(4-picolyl)amino]-2-(4-piper idinyl)acetate dihydrochloride (4 g, 6.87 mmol) and triethyl amine (1.73 g, 17.17 mmol) in methylene chloride (40 ml) is added and the reaction mixture is stirred at room temperature for 1 hour. The reaction mixture is diluted with methylene chloride, washed with saturated aqueous sodium bicarbonate and brine, dried over sodium sulfate, and concentrated in vacuo. Purification by silica gel chromatography (50% ethyl acetate in hexanes then 2% methanol in methylene chloride) provides benzyl 2-(R)-[(4-methoxybenzenesulfonyl)(4-picolyl)-amino]-2-[(N-(2-(1-naphthyl )-ethoxycarbonyl))-4-piperidinyl] acetate as a white solid.

To a solution of benzyl 2-(R)-[(4-methoxybenzenesulfonyl)(4-picolyl)amino]-2-[(N-(2-(1-naphthyl)-ethoxycarbonyl))-4-piperidiny] acetate (4 g, 6.02 mmol) in ethanol (80 ml) and 1N aqueous hydrochloric acid (18 ml, 18 mmol) purged with nitrogen is added 10% palladium on carbon (0.4 g) and the reaction mixture is hydrogenated in a Parr apparatus for 13 hours at room temperature under 50 psi. hydrogen (Note: in every other example described afterward, this hydrogenation step is carried under 1 atm hydrogen instead of 50 psi). The reaction mixture is filtered through celite and concentrated in vacuo to give 2-(R)-[(4-methoxybenzenesulfonyl)(4-picolyl)amino]-2-[(N-(2-(1-naphthyl)-ethoxycarbonyl))-4-piperidinyl] acetic acid which is used without further purification in the next step.

To a solution of the crude 2-(R)-[(4-methoxybenzenesulfonyl)(4-picolyl)amino]-2-[(N-(2-(1-naphthyl)-ethoxycarbonyl))-4-piperidinyl] acetic acid (6.02 mmol) in methylene chloride (150 ml) is added O-t-butylhydroxylamine (2.27 g, 18.06 mmol), N-methylmorpholine (3.65 g, 36.12 mmol), 1-hydroxy-7-azabenzotriazole (819 mg, 6.02 mmol) and 1-ethyl-3-(3-dimethylaminopropyl)carbodiimide hydrochloride (1.5 g, 7.83 mmol). The reaction mixture is stirred at room temperature for 1.5 hours, diluted with ethyl acetate and washed with water. The aqueous layer is extracted with ethyl acetate, the combined organic layers are washed with brine, dried over sodium sulfate, and concentrated in vacuo. The crude product is purified by silica gel chromatography (2% methanol in methylene chloride) to provide N-(t-butyloxy)-2-(R)-[(4-methoxybenzenesulfonyl) (4-picolyl)amino]-2-[(N-(2-(1-naphthyl)-ethoxycarbonyl))-4-piperidinyl]acetamide (3 g).

(b) Similarly prepared is N-hydroxy-2-(R)-[(4-methoxybenzenesulfonyl) (4-picolyl)amino]-2-[(N-(2-phenyl-ethoxycarbonyl))-4-piperidinyl]acetamide hydrochloride, m.p. 138°–140° C., by coupling benzyl 2-(R) -[(4-methoxybenzenesulfonyl) (4-picolyl)amino]-2-(4-piperidinyl)acetate dihydrochloride with 2-phenylethyl alcohol using di(2-pyridyl) carbonate, and by carrying out the subsequent steps similarly as described above.

(c) Similarly prepared is N-hydroxy-2-(R)-[(4-methoxybenzenesulfonyl)(4-picolyl)amino]-2-[(N-(2-(2-naphthyl)-ethoxycarbonyl))-4-piperidinyl]acetami de hydrochloride, m.p. >149° C. (dec), by coupling benzyl 2-(R)-[(4-methoxybenzenesulfonyl) (4-picolyl)amino]-2-(4-piperidinyl)acetate dihydrochloride with 2-(2-naphthyl)-ethyl alcohol using di(2-pyridyl) carbonate, and by carrying out the subsequent steps similarly as described above.

(d) Similarly prepared is N-hydroxy-2-(R)-[(4-methoxybenzenesulfonyl) (4-picolyl)amino]-2-[(N-(2-(1-(2-methylnaphthyl))-ethoxycarbonyl))-4-piperidinyl]acet amide hydrochloride, m.p. 158°–160° C., by coupling benzyl 2-(R)-[(4-methoxybenzenesulfonyl)(4-picolyl)amino]-2-(4-piperidinyl)acetate dihydrochloride with 2-(1-(2-methylnaphthyl))-ethyl alcohol using di(2-pyridyl) carbonate, and by carrying out the subsequent steps similarly as described above.(e) Similarly prepared is N-hydroxy-2-(R)-[(4-methoxybenzenesulfonyl) (4-picolyl)amino]-2-[(N-(2-(1-(2-methoxynaphthyl))-ethoxycarbonyl))-4-piperidinyl]acetamide hydrochloride, m.p. 180°–182° C., by coupling benzyl 2-(R)-[(4-methoxybenzenesulfonyl) (4-picolyl)amino]-2-(4-piperidinyl)acetate dihydrochloride with 2-(1-(2-methoxynaphthyl))ethyl alcohol using di(2-pyridyl) carbonate, and by carrying out the subsequent steps similarly as described above.

(f) Similarly prepared is N-hydroxy-2-(R)-[(4-methoxybenzenesulfonyl) (4-picolyl)amino]-2-[(N-(3-phenylpropoxycarbonyl))-4-piperidinyl]acetamide hydrochloride, m.p. >155° C. (dec), by coupling benzyl 2-(R)-[(4-methoxybenzenesulfonyl) (4-picolyl)amino]-2-(4-piperidinyl)acetate dihydrochloride with 3-phenylpropanol using di(2-pyridyl) carbonate, and by carrying out the subsequent steps similarly as described above.

(g) Similarly prepared is N-hydroxy-2-(R)-[(4-methoxybenzenesulfonyl) (4-picolyl)amino]-2-[(N-(3-(4-methylphenyl)propoxycarbonyl))-4-piperidinyl]acetamide hydrochloride, m.p. >145° C. (dec), by coupling benzyl 2-(R)-[(4-methoxybenzenesulfonyl)(4-picolyl)amino]-2-(4-piperidinyl)acetate dihydrochloride with 3-(4-methylphenyl)-propyl alcohol using di(2-pyridyl)carbonate, and by carrying out the subsequent steps similarly as described above.

(h) Similarly prepared is N-hydroxy-2-(R)-[(4-methoxybenzenesulfonyl) (4-picolyl)amino]-2-[(N-((2,2-dimethyl-3-phenyl)-propoxycarbonyl)-4-piperidinyl] acetamide hydrochloride, m.p. >147° C. (dec), by coupling benzyl 2-(R)-[(4-methoxybenzenesulfonyl) (4-picolyl)amino]-2-(4-piperidinyl)acetate dihydrochloride with (2,2-dimethyl-3-phenyl)-propyl alcohol using di(2-pyridyl) carbonate, and by carrying out the subsequent steps similarly as described above.

(i) Similarly prepared is N-hydroxy-2-(R)-[(4-methoxybenzenesulfonyl) (4-picolyl)amino]-2-[(N-(4-phenylbutoxycarbonyl))-4-piperidinyl]acetamide hydrochloride, m.p. >151° C. (dec), by coupling benzyl 2-(R)-[(4-methoxybenzenesulfonyl) (4-picolyl)amino]-2-(4-piperidinyl)acetate dihydrochloride with 4-phenylbutanol using di(2-pyridyl) carbonate, and by carrying out the subsequent steps similarly as described above.

(j) Similarly prepared is N-hydroxy-2-(R)-[(4-methoxybenzenesulfonyl) (4-picolyl)amino]-2-[(N-(3-(1-naphthyl)-propoxycarbonyl))-4-piperidinyl]acetamide hydrochloride as a white solid, m.p. 145°–147° C., by coupling benzyl 2-(R)-[(4-methoxybenzenesulfonyl)(4-picolyl)amino]-2-(4-piperidinyl)acetate dihydrochloride with 3-(1-naphthyl)-propyl alcohol using di(2-pyridyl) carbonate, and by carrying out the subsequent steps similarly as described above. (k) Similarly prepared is N-hydroxy-2-(R)-[(4-methoxybenzenesulfonyl) (4-picolyl)amino]-2-[(N-(2-cyclohexyl-ethoxycarbonyl))-4-piperidinyl]acetamide hydrochloride, m.p. >157° C. (dec), by coupling benzyl 2-(R)-[(4-methoxybenzenesulfonyl) (4-picolyl)amino]-2-(4-piperidinyl)acetate dihydrochloride with 2-cyclohexylethanol using di(2-pyridyl) carbonate, and by carrying out the subsequent steps similarly as described above.

(l) Similarly prepared is N-hydroxy-2-(R)-[(4-methoxybenzenesulfonyl) (4-piclyl)amino]-2-[( N-(2-(4-biphenyl)-ethoxycarbonyl))-4-piperidinyl]acetamide hydrochloride, m.p. >160° C. (dec), by coupling benzyl 2-(R)-[(4-methoxybenzenesulfonyl) (4-picolyl)amino]-2-(4-piperidinyl)acetate dihydrochloride with 2-(4-biphenyl)-ethyl alcohol using di(2-pyridyl) carbonate, and by carrying out the subsequent steps similarly as described above.

(m) Similarly prepared is N-hydroxy-2-(R)-[(4-methoxybenzenesulfonyl) (4-picolyl)amino]-2-[(N-2-(1-adamantyl)-ethoxycarbonyl))-4-piperidinyl]acetamide hydrochloride, m.p. >167° C. (dec), by coupling benzyl 2-(R)-[(4-methoxybenzenesulfonyl) (4-picolyl)amino]-2-(4-piperidinyl)acetate dihydrochloride with 2-(1-adamantyl)-ethyl alcohol using di(2-pyridyl) carbonate, and by carrying out the subsequent steps similarly as described above.

(n) Similarly prepared is N-hydroxy-2-(R)-[(4-methoxybenzenesulfonyl) (4-picolyl)amino]-2-[(N-(2,2-(diphenyl)-ethoxycarbonyl))-4-piperidinyl]acetamide hydrochloride, m.p. 175°–178° C., by coupling benzyl 2-(R)-[(4-methoxybenzenesulfonyl) (4-picolyl)amino]-2-(4-piperidinyl)acetate dihydrochloride with 2,2-diphenylethyl alcohol using di(2-pyridyl) carbonate, and by carrying out the subsequent steps similarly as described above.

(o) Similarly prepared is N-hydroxy-2-(R)-[(4-methoxybenzenesulfonyl) (4-picolyl)amino]-2-[(N-(2-(N-(2,3-dimethyl)-indolyl)-ethoxycarbonyl))-4-piperidinyl] acetamride hydrochloride, m.p. 178°–180° C., by coupling benzyl 2-(R)-[(4-methoxybenzenesulfonyl) (4-picolyl) amino]-2-(4-piperidinyl)acetate dihydrochloride with 2-(N-(2,3-dimethyl)-indolyl)-ethyl alcohol using di(2-pyridyl) carbonate, and by carrying out the subsequent steps similarly as described above.

(p) Similarly prepared is N-hydroxy-2-(R)-[(4-methoxybenzenesulfonyl) (4-picolyl)amino]-2-[(N-(2-(N-phthalimido)-ethoxycarbonyl))-4-piperidinyl]acetamide hydrochloride, m.p. >167° C. (dec), by coupling benzyl 2-(R)-[(4-methoxybenzenesulfonyl)(4-picolyl)amino]-2-(4-piperidinyl)acetate dihydrochloride with 2-(N-phthalimidoyl)-ethyl alcohol using di(2-pyridyl) carbonate, and by carrying out the subsequent steps similarly as described above.

(q) Similarly prepared is N-hydroxy-2-(R)-[(4-methoxybenzenesulfonyl) (4-picolyl)amino]-2-[(N-(2-(N-(2H-1,4-benzoxazin-3-onyl))-ethoxycarbonyl))-4-piperidinyl]acetamide hydrochloride, m.p. >163° C. (dec), by coupling benzyl 2-(R)-[(4-methoxybenzenesulfonyl)(4-picolyl)amino]-2-(4-piperidinyl)acetate dihydrochloride with 2-(N-(2H-1,4-benzoxazin-3-onyl))-ethyl alcohol using di(2-pyridyl) carbonate, and by carrying out the subsequent steps similarly as described above.

(r) Similarly prepared is N-hydroxy-2-(R)-[(4-methoxybenzenesulfonyl) (4-picolyl)amino]-2-[(N-(2-(4-morpholino)-ethoxycarbonyl))-4-piperidinyl]acetamide dihydrochloride, m.p. >147° C. (dec), by coupling benzyl 2-(R)-[(4-methoxybenzenesulfonyl)(4-picolyl)amino]-2-(4-piperidinyl)acetate dihydrochloride with 2-(4-morpholino)-ethyl alcohol using di(2-pyridyl)carbonate, and by carrying out the subsequent steps similarly as described above.

EXAMPLE 2

(a) Similarly prepared as described in example 1 is N-hydroxy-2-(R)-[(4-methoxybenzenesulfonyl) (4-picolyl) amino]-2-[(N-isopropoxycarbonyl)-4-piperidinyl]acetamide hydrochloride, m.p. >172° C. (dec). The required intermediate benzyl 2-(R)-[(4-methoxybenzenesulfonyl) (4-picolyl) amino]-2-[(N-isopropoxycarbonyl)-4-piperidinyl] acetate is prepared as follows:

To a solution of benzyl 2-(R)-[(4-methoxybenzenesulfonyl)(4-picolyl)amino]-2-(4-piperidinyl)acetate dihydrochloride (500 mg, 1.04 mmol) in methylene chloride (20 ml) cooled to 0° C. is added triethylamine (471 mg, 4.67 mmol) followed by isopropyl chloroformate (140 mg, 1.14 mmol). The reaction mixture is stirred at 0° C. for 15 minutes and at room temperature for 15 minutes. The reaction mixture is diluted with methylene chloride and saturated aqueous sodium bicarbonate. The organic layer is separated and the aqueous layer is extracted with methylene chloride. The combined organic layers are dried over sodium sulfate and concentrated in vacuo. Purification by silica gel chromatography (ethyl acetate) provides benzyl 2-(R)-[(4-methoxybenzenesulfonyl) (4-picolyl)amino]-2-[(N-isopropoxycarbonyl)-4-piperidinyl] acetate. The remainder of the synthesis is carried out similarly as described in example 1.

(b) Similarly prepared is N-hydroxy-2-(R)-[(4-methoxybenzenesulfonyl) (4-picolyl)amino]-2-[(N-propoxycarbonyl)-4-piperidinyl]acetamide hydrochloride, m.p. >167° C. (dec), by acylation of benzyl 2-(R)-[(4-methoxybenzenesulfonyl) (4-picolyl)amino]-2-(4-piperidinyl)acetate dihydrochloride with n-propyl chloroformate, and by carrying out the subsequent steps similarly as described above.

(c) Similarly prepared is N-hydroxy-2-(R)-[(4-methoxybenzenesulfonyl) (4-picolyl)amino]-2-[(N-isobutoxycarbonyl)-4-piperidinyl]acetamide hydrochloride, m.p. >162° C. (dec), by acylation of benzyl 2-(R)-[(4-methoxybenzenesulfonyl)(4-picolyl)amino]-2-(4-piperidinyl)acetate dihydrochloride with isobutyl chloroformate, and by carrying out the subsequent steps similarly as described above.

(d) Similarly prepared is N-hydroxy-2-(R)-[(4-methoxybenzenesulfonyl) (4-picolyl)amino]-2-[(N-butoxycarbonyl)-4-piperidinyl]acetamide hydrochloride, m.p. 152°–154° C., by acylation of benzyl 2-(R)-[(4-methoxybenzenesulfonyl)(4-picolyl)amino]-2-(4-piperidinyl)acetate dihydrochloride with n-butyl chloroformate, and by carrying out the subsequent steps similarly as described above.

(e) Similarly prepared is N-hydroxy-2-(R)-[(4-methoxybenzenesulfonyl) (4-picolyl)amino]-2-[(N-(2-methoxy)-ethoxycarbonyl)-4-piperidinyl]acetamide hydrochloride, m.p. 153°–158° C., by acylation of benzyl 2-(R)-[(4-methoxybenzenesulfonyl) (4-picolyl)amino]-2-(4-piperidinyl)acetate dihydrochloride with chloroformic acid 2-methoxyethyl ester, and by carying out the subsequent steps similarly as described above.

(f) Similarly prepared is N-hydroxy-2(R)-[(4-methoxybenzenesulfonyl) (4-picolyl)amino]-2-(N-ethoxycarbonyl-4-piperidinyl)-acetamide hydrochloride, m.p. 145°–158° dec.; [a]D+19.83 (c=5.56 mg/ml, CH$_3$OH).

EXAMPLE 3

(a) Similarly prepared as described in example 1 is N-hydroxy-2-(R)-[(4-methoxybenzenesulfonyl) (4-picolyl) amino]-2-[(N-(2-(2,3-methylenedioxyphenyl)-ethoxycarbonyl))-4-piperidinyl]acetamide trifluoroacetic acid salt, m.p. 158° C., by coupling benzyl 2-(R)-[(4-methoxybenzenesulfonyl)(4-picolyl)amino]-2-(4- piperidinyl)acetate dihydrochloride with 2-(2,3-methylenedioxyphenyl)-ethyl alcohol using di(2-pyridyl) carbonate, and by carrying out the final steps as follows:

To a solution of benzyl 2-(R)-[(4-methoxybenzenesulfonyl)(4-picolyl)amino]-2-[(N-(2-(2,3-methylenedioxyphenyl)-ethoxycarbonyl))-4-piperidinyl] acetate (465 mg, 0.66 mmol) in ethanol (25 ml) and 1N aqueous hydrochloric acid (1.98 ml, 1.98 mmol) purged with nitrogen is added 10% palladium on carbon (45 mg) and the reaction mixture is hydrogenated at room temperature under 1 atm hydrogen for 9 hours. The reaction mixture is filtered through celite and concentrated in vacuo to provide the crude acid which is used in the next step without further purification.

To a solution of the crude 2-(R)-[(4-methoxybenzenesulfonyl)(4-picolyl)amino]-2-[(N-(2-(2,3-methylenedioxyphenyl)-ethoxycarbonyl))-4-piperidinyl] acetic acid (0.66 mmol) in methylene chloride (35 ml) is added O-tritylhydroxylamine (547 mg, 1.98 mmol), N-methylmorpholine (0.44 ml, 3.97 mmol), 1-hydroxy-7-azabenzotriazole (90 mg, 0.66 mmol) and 1-ethyl-3-(3-dimethylaminopropyl)carbodiimide hydrochloride (165 mg, 0.86 mmol). The reaction mixture is stired at room temperature for 18 hours, diluted with ethyl acetate and washed with water. The aqueous layer is extracted with ethyl acetate, the combined organic layers are washed with brine, dried over sodium sulfate, and concentrated in vacuo. The crude product is purified by silica gel chromatography (2% to 4% methanol in methylene chloride) to provide N-(trityl-oxy)-2-(R)-[(4-methoxybenzenesulfonyl) (4-picolyl)amino]-2-[(N-(2-(2,3-methylenedioxy-phenyl)-ethoxycarbonyl))-4-piperidinyl]acetamide.

To a solution of N-(trityloxy)-2-(R)-[(4-methoxybenzenesulfonyl) (4-picolyl)amino]-2-[(N-(2-(2,3-methylenedioxyphenyl)-ethoxycarbonyl))-4-piperidinyl] acetamide (468 mg, 0.54 mmol) in methylene chloride (10 ml) cooled to 0° C. is added triethyl silane (0.17 ml, 1.08 mmol) followed by slow addition of trifluoroacetic acid (0.33 ml, 4.31 mmol). After stirring at 0° C. for 5 minutes, the solvent is removed in vacuo, at room temperature. The resulting white solid is dried on high vacuum for 1 hour and dissolved in the minimum amount of methylene chloride (ca. 2.5 ml). A mixture of diethyl ether (ca. 5 ml) and pentane (ca. 2.5 ml) is slowly added and the resulting white precipitate is triturated, filtered and washed with pentane (Note: this precipitation process must be repeated a second time if high purity is not obtained after the first attempt), to provide N-hydroxy-2-(R)-[(4-methoxybenzenesulfonyl)(4-picolyl) amino]-2-[(N-(2-(2,3-methylenedioxyphenyl)-ethoxycarbonyl))-4-piperidinyl]acetamide trifluoroacetic acid salt.

(b) Similarly prepared is N-hydroxy-2-(R)-[(4-methoxybenzenesulfonyl) (4-picolyl)amino]-2-[(N-(2-(3-(1, 2-dimethylindolyl))-ethoxycarbonyl))-4-piperidinyl] acetamide trifluoroacetic acid salt, m.p. 175°–178° C., by coupling benzyl 2-(R)-[(4-methoxybenzenesulfonyl) (4-picolyl)amino]-2-(4-piperidinyl)acetate dihydrochloride with 2-(3-(1,2-dimethyl)-indolyl)-ethyl alcohol using di(2-pyridyl) carbonate, and by carrying out the final steps as described above.

(c) Similarly prepared is N-hydroxy-2-(R)-[(4-methoxybenzenesulfonyl) (4-picolyl)amino]-2-[(N-(2-(4-quinolinyl)-ethoxycarbonyl)))-4-piperidinyl]acetamide trifluoroacetic acid di-salt, m.p. 148° C., by coupling benzyl 2-(R)-[(4-methoxybenzenesulfonyl)(4-picolyl)amino]-2-(4-piperidinyl)acetate dihydrochloride with 2-(4-quinolinyl)-ethyl alcohol using di(2-pyridyl) carbonate, and by carrying out the final steps as described above.

(d) Similarly prepared is N-hydroxy-2-(R)-[(4-methoxybenzenesulfonyl) (4-picolyl)amino]-2-[(N-(3-(4-quinolinyl)-propoxycarbonyl)))-4-piperidinyl]acetamide trifluoroacetic acid di-salt, m.p. 135° C., by coupling benzyl 2-(R)-[(4-methoxybenzenesulfonyl) (4-picolyl)amino]-2-(4-piperidinyl)acetate dihydrochloride with 3-(4-quinolinyl)-propyl alcohol using di(2-pyridyl) carbonate, and by carrying out the final steps as described above.

(e) Similarly prepared is N-hydroxy-2-(R)-[(4-methoxybenzenesulfonyl) (4-picolyl)amino]-2-[(N-(2-(N-(1,2,3,4-tetrahydroquinolinyl)-ethoxycarbonyl))-4-piperidinyl]acetamide trifluoroacetic acid salt, m.p. >146° C. (dec), by coupling benzyl 2-(R)-[(4-methoxybenzenesulfonyl)(4-picolyl)amino]-2-(4-piperidinyl)acetate dihydrochloride with 2-(N-(1,2,3,4-tetrahydroquinolinyl)-ethyl alcohol using di(2-pyridyl) carbonate, and by carrying out the final steps as described above.

(f) Similarly prepared is N-hydroxy-2-(R)-[(4-methoxybenzenesulfonyl) (4-picolyl)amino]-2-[(N-(2-(N-(2-benzoxazolinonyl))-ethoxycarbonyl))-4-piperidinyl] acetamide trifluoroacetic acid salt, m.p. >167° C. (dec), by coupling benzyl 2-(R)-[(4-methoxybenzenesulfonyl) (4-picolyl)amino]-2-(4-piperidinyl)acetate dihydrochloride with 2-(N-(2-benzoxazolinonyl))-ethyl alcohol using di(2-pyridyl) carbonate, and by carrying out the final steps as described above.

(g) Similarly prepared is N-hydroxy-2-(R)-[(4-methoxybenzenesulfonyl) (4-picolyl)amino]-2-[(N-(2-(2-benzotriazolyl)-ethoxycarbonyl))-4-piperidinyl]acetamide trifluoroacetic acid salt, m.p. 122°–125° C., by coupling benzyl 2-(R)-[(4-methoxybenzenesulfonyl)(4-picolyl) amino]-2-(4-piperidinyl)acetate dihydrochloride with 2-(2-benzotriazolyl)-ethyl alcohol using di(2-pyridyl)carbonate, and by carrying out the final steps as described above.

(h) Similarly prepared is N-hydroxy-2-(R)-[(4-methoxybenzenesulfonyl) (4-picolyl)amino]-2-[(N-(2-(2-pyridyl)-ethoxycarbonyl))-4-piperidinyl]acetamide trifluoroacetic acid di-salt, m.p. 165° C., by coupling benzyl 2-(R)-[(4-methoxybenzenesulfonyl) (4-picolyl)amino]-2-(4-piperidinyl)acetate dihydrochloride with 2-(2-pyridyl)-ethyl alcohol using di(2-pyridyl) carbonate, and by carrying out the final steps as described above.

(i) Similarly prepared is N-hydroxy-2-(R)-[(4-methoxybenzenesulfonyl) (4-picolyl)amino]-2-[(N-(2-(3,4-methylenedioxyphenyl)-ethoxycarbonyl))-4-piperidinyl] acetamide trifluoroacetic acid salt, m.p. 122°–125° C., by coupling benzyl 2-(R)-[(4-methoxybenzenesulfonyl)(4-picolyl)amino]-2-(4-piperidinyl)acetate dihydrochloride with 2-(3,4-methylenedioxyphenyl)-ethyl alcohol using di(2-pyridyl) carbonate, and by carrying out the final steps as described above.

EXAMPLE 4

To a solution of N-(trityloxy)-2-(R)-[(4-methoxybenzenesulfonyl) (4-picolyl)amino]-2-[(N-tert-butoxycarbonyl)-4-piperidinyl]acetamide (205 mg, 0.26 mmol) in methylene chloride (10 ml) cooled to −5° C. is added triethyl silane (0.046 ml, 0.285 mmol) followed by slow addition of trifluoroacetic acid (0.04 ml, 0.52 mmol). After stirring at −5° C. for 15 minutes, the solvent is removed in vacuo, at room temperature. The resulting white solid is dried on high vacuum for 18 hours and dissolved in the minimum amount of methylene chloride (ca. 2.5 ml). A mixture of diethyl ether (ca. 5 ml) and pentane (ca. 2.5 ml) is slowly added and the resulting white precipitate is triturated, filtered and washed with pentane to provide N-hydroxy-2-(R)-[(4-methoxybenzenesulfonyl) (4-picolyl) amino]-2-[(N-tert-butoxycarbonyl)-4-piperidinyl]acetamide trifluoroacetic acid salt, m.p. 168° C.

The starting material is prepared similarly as described before by hydrogenation of benzyl 2-(R)-[(4-methoxybenzenesulfonyl)(4-picolyl)amino]-2-(N-t-BOC-4-piperidinyl) acetate, followed by coupling with O-tritylhydroxylamine using 1-(3-dimethylaminopropyl)-3-ethylcarbodiimide hydrochloride (EDCI).

EXAMPLE 5

To a solution of N-(trityloxy)-2-(R)-[(4-methoxybenzenesulfonyl) (4-picolyl)amino]-2-[(N-tert-butoxycarbonyl)-4-piperidinyl]acetamide (408 mg, 0.52 mmol) in methylene chloride (10 ml) cooled to 0° C. is added triethyl silane (0.165 ml, 1.03 mmol) followed by slow addition of trifluoroacetic acid (0.32 ml, 4.13 mmol). After stirring at 0° C. for 30 minutes, trifluoroacetic acid (2 ml) is added and the reaction mixture is stirred at 0° C. for 10 minutes. The solvent is removed in vacuo, at room temperature. The resulting white solid is dried on high vacuum for 18 hours and dissolved in the minimum amount of methylene chloride (ca. 2.5 ml). A mixture of diethyl ether (ca. 5 ml) and pentane (ca. 2.5 ml) is slowly added and the resulting white precipitate is triturated, filtered and washed with pentane to provide N-hydroxy-2-(R)-[(4-methoxybenzenesulfonyl) (4-picolyl)amino]-2-(4-piperidinyl)acetamide trifluoroacetic acid di-salt, m.p. 165° C.

EXAMPLE 6

(a) Similarly prepared as previously described in the examples is N-hydroxy-2-(R)-[(4-methoxybenzenesulfonyl) (4-picolyl)amino]-2-[(N-(2-thiophenecarbonyl))-4-piperidinyl]acetamide hydrochloride, m.p. >177° C. (dec). The required intermediate benzyl 2-(R)-[(4-methoxybenzenesulfonyl)(4-picolyl)amino]-2-[(N-(2-thiophenecarbonyl))-4-piperidinyl] acetate is prepared as follows: To a solution of benzyl 2-(R)-[(4-methoxybenzenesulfonyl)(4-picolyl)amino]-2-(4-piperidinyl)acetate dihydrochloride (400 mg, 0.69 mmol) in methylene chloride (5 ml) cooled to 0° C. is added triethylamine (0.31 ml, 2.25 mmol) followed by slow addition of a solution of 2-thiophenecarbonyl chloride in methylene chloride (1 ml). The reaction mixture is stirred at 0° C. for 5 minutes, diluted with methylene chloride, washed with saturated aqueous sodium bicarbonate and brine. The organic layer is dried over sodium sulfate and concentrated in vacuo. Purification by silica gel chromatography (ethyl acetate to 2% methanol in ethyl acetate) provides benzyl 2-(R)-[(4-methoxybenzenesulfonyl) (4-picolyl)amino]-2-[(N-(2-thiophenecarbonyl))-4-piperidinyl] acetate. The remainder of the synthesis is carried out similarly as described in example 1.

(b) Similarly prepared is N-hydroxy-2-(R)-[(4-methoxybenzenesulfonyl) (4-picolyl)amino]-2-[(N-propionyl)-4-piperidinyl]acetamide hydrochloride, m.p. >179° C. (dec), by acylation of benzyl 2-(R)-[(4-methoxybenzenesulfonyl)(4-picolyl)amino]-2-(4-piperidinyl)acetate dihydrochloride with propionyl chloride, and by carrying out the subsequent steps similarly as described above.

(c) Similarly prepared is N-hydroxy-2-(R)-[(4-methoxybenzenesulfonyl) (4-picolyl)amino]-2-[(N-isobutyryl)-4-piperidinyl]acetamide hydrochloride, m.p. >173° C. (dec), by acylation of benzyl 2-(R)-[(4-methoxybenzenesulfonyl)(4-picolyl)amino]-2-(4-piperidinyl)acetate dihydrochloride with isobutyryl chloride, and by carrying out the subsequent steps similarly as described above.

(d) Similarly prepared is N-hydroxy-2-(R)-[(4-methoxybenzenesulfonyl) (4-picolyl)amino]-2-[(N-pivaloyl)-4-piperidinyl]acetamide hydrochloride, m.p. >167° C. (dec), by acylation of benzyl 2-(R)-[(4-methoxybenzenesulfonyl)(4-picolyl)amino]-2-(4-piperidinyl)acetate dihydrochloride with pivaloyl chloride, and by carrying out the subsequent steps similarly as described above.

(e) Similarly prepared is N-hydroxy-2-(R)-[(4-methoxybenzenesulfonyl) (4-picolyl)amino]-2-[(N-butyryl)-4-piperidinyl]acetamide hydrochloride, m.p. 170° C., by acylation of benzyl 2-(R)-[(4-methoxybenzenesulfonyl)(4-picolyl)amino]-2-(4-piperidinyl)acetate dihydrochloride with butyryl chloride, and by carrying out the subsequent steps similarly as described above.

(f) Similarly prepared is N-hydroxy-2-(R)-[(4-methoxybenzenesulfonyl) (4-picolyl)amino]-2-[(N-isovaleryl)-4-piperidinyl]acetamide hydrochloride, m.p. 166°–167° C., by acylation of benzyl 2-(R)-[(4-methoxybenzenesulfonyl)(4-picolyl)amino]-2-(4-piperidinyl)acetate dihydrochloride with isovaleryl chloride, and by carrying out the subsequent steps similarly as described above.

(g) Similarly prepared is N-hydroxy-2-(R)-[(4-methoxybenzenesulfonyl) (4-picolyl)amino]-2-[(N-valeryl)-4-piperidinyl]acetamide hydrochloride, m.p. >167° C. (dec), by acylation of benzyl 2-(R)-[(4-methoxybenzenesulfonyl)(4-picolyl)amino]-2-(4-piperidinyl)acetate dihydrochloride with valeryl chloride, and by carrying out the subsequent steps similarly as described above.

EXAMPLE 7

Similarly prepared as described in example 6 is N-hydroxy-2-(R)-[(4-methoxybenzenesulfonyl) (4-picolyl)amino]-2-[(N-acetyl)-4-piperidinyl]acetamide hydrochloride, m.p. >165° C. (dec), by acylation of benzyl 2-(R)-[(4-methoxybenzenesulfonyl) (4-picolyl)amino]-2-(4-piperidinyl)acetate dihydrochloride with acetic anhydride, and by carrying out the subsequent steps similarly as described above.

EXAMPLE 8

Similarly prepared as described in example 6 is N-hydroxy-2-(R)-[(4-methoxybenzenesulfonyl) (4-picolyl) amino]-2-[(N-(4-phenylbutyryl))-4-piperidinyl]acetamide hydrochloride, m.p. 170° C. The required intermediate benzyl 2-(R)-[(4-methoxybenzenesulfonyl) (4-picolyl)amino]-2-[(N-(4-phenylbutyryl))-4-piperidinyl] acetate is prepared as follows: To a solution of benzyl 2-(R)-[(4-methoxybenzenesulfonyl) (4-picolyl)amino]-2-(4-piperidinyl)acetate dihydrochloride (858 mg, 1.78 mmol) in methylene chloride (25 ml) is added N-methylmorpholine (0.98 ml, 8.9 mmol), 1-hydroxy-7-azabenzotriazole (242 mg, 1.78 mmol), 4-phenylbutyric acid (322 mg, 1.96 mmol) and 1-ethyl-3-(3-dimethylaminopropyl)carbodiimide hydrochloride (683 mg, 3.56 mmol). The reaction mixture is stirred at room temperature for 1.5 hours. The solvent is removed in vacuo and the residue is taken in ethyl acetate. The organic layer is washed with water and brine, dried over magnesium sulfate, and concentrated in vacuo. Purification by silica gel chromatography (3% to 5% methanol in methylene chloride) provides 2-(R)-[(4-methoxybenzenesulfonyl)(4-picolyl)amino]-2-[(N-(4-phenylbutyryl))-4-piperidinyl] acetate.

EXAMPLE 9

(a) Similarly prepared as described in example 1 is N-hydroxy-2-(R)-[(4-methoxybenzenesulfonyl) (4-picolyl)amino]-2-[(N-(4-methylphenyl)-sulfonyl)-4-piperidinyl]acetamide hydrochloride, m.p. >172° C. (dec). The required intermediate benzyl 2-(R)-[(4-methoxybenzenesulfonyl)(4-picolyl)amino]-2-[(N-(4-methylphenyl)sulfonyl)-4-piperidinyl] acetate is prepared as follows: To a solution of benzyl 2-(R)-[(4-methoxybenzenesulfonyl)(4-picolyl)amino]-2-(4-piperidinyl)acetate dihydrochloride (500 mg, 1.04 mmol) in methylene chloride (20 ml) cooled to 0° C. is added triethylamine (368 mg, 3.63 mmol) and tosyl chloride (208 mg, 1.09 mmol). The reaction mixture is stirred at 0° C. for 10 minutes. The reaction mixture is quenched with saturated aqueous sodium bicarbonate, the organic layer is separated. The aqueous layer is extracted with methylene chloride and the combined organic layer is washed with brine, dried over sodium sulfate, and concentrated in vacuo. Purification by silica gel chromatography (75% to 100% ethyl acetate in hexanes) provides benzyl 2-(R)-[(4-methoxybenzenesulfonyl)(4-picolyl)amino]-2-[(N-(4-methylphenyl)sulfonyl)-4-piperidinyl]acetate. The remaining of the synthesis is carried out similarly as described in example 1.

(b) Similarly prepared is N-hydroxy-2-(R)-[(4-methoxybenzenesulfonyl) (4-picolyl)amino]-2-[(N-methylsulfonyl)-4-piperidinyl]acetamide hydrochloride, m.p. 176°–179° C., by sulfonylation of benzyl 2-(R)-[(4-methoxybenzenesulfonyl)(4-picolyl)amino]-2-(4-piperidinyl)acetate dihydrochloride with methylsulfonyl chloride, and by carrying out the subsequent steps similarly as described above.

(c) Similarly prepared is N-hydroxy-2-(R)-[(4-methoxybenzenesulfonyl) (4-picolyl)amino]-2-[(N-isopropylsulfonyl)-4-piperidinyl]acetamide hydrochloride, m.p. >162° C. (dec), by sulfonylation of benzyl 2-(R)-[(4-methoxybenzenesulfonyl) (4-picolyl)amino]-2-(4-piperidinyl)acetate dihydrochloride with isopropylsulfonyl chloride, and by carrying out the subsequent steps similarly as described above.

(d) Similarly prepared is N-hydroxy-2-(R)-[(4-methoxybenzenesulfonyl) (4-picolyl)amino]-2-[(N-butylsulfonyl)-4-piperidinyl]acetamide hydrochloride, m.p. 164°–166° C., by sulfonylation of benzyl 2-(R)-[(4-methoxybenzenesulfonyl) (4-picolyl)amino]-2-(4-piperidinyl)acetate dihydrochloride with butylsulfonyl chloride, and by carrying out the subsequent steps similarly as described above.

(e) Similarly prepared is N-hydroxy-2-(R)-[(4-methoxybenzenesulfonyl) (4-picolyl)amino]-2-[(N-phenethylsulfonyl)-4-piperidinyl]acetamide hydrochloride, m.p. >154° C. (dec), by sulfonylation of benzyl 2-(R)-[(4-methoxybenzenesulfonyl) (4-picolyl)amino]-2-(4-piperidinyl)acetate dihydrochloride with phenethylsulfonyl chloride, and by carrying out the subsequent steps similarly as described above.

EXAMPLE 10

Similarly prepared as described in example 1 is N-hydroxy-2-(R)-[(4-methoxybenzenesulfonyl) (4-picolyl)amino]-2-[(N-dimethylaminosulfonyl)-4-piperidinyl] acetamide hydrochloride, m.p. >175° C. (dec). The required intermediate benzyl 2-(R)-[(4-methoxybenzenesulfonyl) (4-picolyl)amino]-2-[(N-dimethylaminosulfonyl)-4-piperidinyl] acetate is prepared as follows: To a solution of benzyl 2-(R)-[(4-methoxybenzenesulfonyl) (4-picolyl)amino]-2-(4-piperidinyl)acetate dihydrochloride (400 mg, 0.83 mmol) in methylene chloride (20 ml) cooled to 0° C. is added triethylamine (293 mg, 2.90 mmol) and dimethylsulfamoyl chloride. The reaction mixture is allowed to warm to room temperature and stirred at room temperature for 5 hours. The reaction mixture is quenched with saturated aqueous sodium bicarbonate, the organic layer is extracted. The aqueous layer is extracted with methylene chloride and the combined organic layer is washed with brine, dried over sodium sulfate, and concentrated in vacuo. Purification by silica gel chromatography (2% methanol in methylene chloride) provides benzyl 2-(R)-[(4-methoxybenzenesulfonyl)(4-picolyl)amino]-2-[(N-dimethylaminosulfonyl)-4-piperidinyl] acetate. The remainder of the synthesis is carried out similarly as described in example 1.

EXAMPLE 11

(a) Similarly prepared as described in example 1 is N-hydroxy-2-(R)-[(4-methoxybenzenesulfonyl) (4-picolyl)amino]-2-[(N-methylaminocarbonyl)-4-piperidinyl] acetamide hydrochloride, m.p. 171° C. The required intermediate benzyl 2-(R)-[(4-methoxybenzenesulfonyl) (4-picolyl)amino]-2-[(N-methylaminocarbonyl)-4-piperidinyl] acetate is prepared as follows: To a solution of benzyl 2-(R)-[(4-methoxybenzenesulfonyl) (4-picolyl)amino]-2-(4-piperidinyl)acetate dihydrochloride (400 mg, 0.83 mmol) in methylene chloride (20 ml) is added triethylamine (293 mg, 2.90 mmol) and methyl isocyanate (52 mg, 0.91 mmol). The reaction mixture is stirred at room temperature for 10 minutes. The reaction mixture is quenched with saturated aqueous sodium bicarbonate, the organic layer is extracted. The aqueous layer is extracted with methylene chloride and the combined organic layer is washed with brine, dried over sodium sulfate, and concentrated in vacuo to provide benzyl 2-(R)-[(4-methoxybenzenesulfonyl)(4-picolyl)amino]-2-[(N-methylaminocarbonyl)-4-piperidinyl] acetate. The remainder of the synthesis is carried out similarly as described in example 1.

(b) Similarly prepared is N-hydroxy-2-(R)-[(4-methoxybenzenesulfonyl) (4-picolyl)amino]-2-[(N-ethylaminocarbonyl)-4-piperidinyl]acetamide hydrochloride, m.p. >172° C. (dec), by reaction of benzyl 2-(R)-[(4-methoxybenzenesulfonyl)(4-picolyl)amino]-2-(4-piperidinyl)acetate dihydrochloride with ethyl isocyanate, and by carrying out the subsequent steps similarly as described above.

(c) Similarly prepared is N-hydroxy-2-(R)-[(4-methoxybenzenesulfonyl) (4-picolyl)amino]-2-[(N-propylaminocarbonyl)-4-piperidinyl]acetamide hydrochloride, m.p. >167° C. (dec), by reaction of benzyl 2-(R)-[(4-methoxybenzenesulfonyl) (4-picolyl)amino]-2-(4-piperidinyl)acetate dihydrochloride with propyl isocyanate, and by carrying out the subsequent steps similarly as described above.

(d) Similarly prepared is N-hydroxy-2-(R)-[(4-methoxybenzenesulfonyl) (4-picolyl)amino]-2-[(N-isopropylaminocarbonyl)-4-piperidinyl]acetamide hydrochloride, m.p. >170° C. (dec), by reaction of benzyl 2-(R)-[(4-methoxybenzenesulfonyl) (4-picolyl)amino]-2-(4-piperidinyl)acetate dihydrochloride with isopropyl isocyanate, and by carrying out the subsequent steps similarly as described above.

(e) Similarly prepared is N-hydroxy-2-(R)-[(4-methoxybenzenesulfonyl) (4-picolyl)amino]-2-[(N-butylaminocarbonyl)-4-piperidinyl]acetamide hydrochloride, m.p. >175° C. (dec), by reaction of benzyl 2-(R)-[(4-methoxybenzenesulfonyl) (4-picolyl)amino]-2-(4-piperidinyl)acetate dihydrochloride with butyl isocyanate, and by carrying out the subsequent steps similarly as described above. (f) Similarly prepared is N-hydroxy-2-(R)-[(4-methoxybenzenesulfonyl) (4-picolyl)amino]-2-[(N-benzylaminocarbonyl)-4-piperidinyl] acetamide hydrochloride, m.p. >163° C. (dec), by reaction of benzyl 2-(R)-[(4-methoxybenzenesulfonyl)(4-picolyl)amino]-2-(4-piperidinyl)acetate dihydrochloride with benzyl isocyanate, and by carrying out the subsequent steps similarly as described above.

(h) Similarly prepared is N-hydroxy-2-(R)-[(4-methoxybenzenesulfonyl) (4-picolyl)amino]-2-[(N-benzoylaminocarbonyl)-4-piperidinyl]acetamide hydrochloride, m.p. >149° C. (dec), by reaction of benzyl 2-(R)-[(4-methoxybenzenesulfonyl) (4-picolyl)amino]-2-(4-piperidinyl)acetate dihydrochloride with benzoyl isocyanate, and by carrying out the subsequent steps similarly as described above.

(i) Similarly prepared is N-hydroxy-2-(R)-[(4-methoxybenzenesulfonyl) (4-picolyl)amino]-2-[(N-dimethylaminocarbonyl)-4-piperidinyl]acetamide hydrochloride, m.p. >175° C. (dec), by reaction of benzyl 2-(R)-[(4-methoxybenzenesulfonyl) (4-picolyl)amino]-2-(4-piperidinyl)acetate dihydrochloride with dimethylcarbamoyl chloride, and by carrying out the subsequent steps similarly as described above.

(j) Similarly prepared is N-hydroxy-2-(R)-[(4-methoxybenzenesulfonyl) (4-picolyl)amino]-2-[(N-diethylaminocarbonyl)-4-piperidinyl]acetamide hydrochloride, m.p. >176° C. (dec), by reaction of benzyl 2-(R)-[(4-methoxybenzenesulfonyl) (4-picolyl)amino]-2-(4-piperidinyl)acetate dihydrochloride with diethylcarbamoyl chloride, and by carrying out the subsequent steps similarly as described above.

(k) Similarly prepared is N-hydroxy-2-(R)-[(4-methoxybenzenesulfonyl) (4-picolyl)amino]-2-[(N-diisopropylaminocarbonyl)-4-piperidinyl]acetamide hydrochloride, m.p. >168° C. (dec), by reaction of benzyl 2-(R)-[(4-methoxybenzenesulfonyl) (4-picolyl)amino]-2-(4-piperidinyl)acetate dihydrochloride with diisopropylcarbamoyl chloride, and by carrying out the subsequent steps similarly as described above.

(1) Similarly prepared is N-hydroxy-2-(R)-[(4-methoxybenzenesulfonyl) (4-picolyl)amino]-2-[(N-methyl-N-phenylaminocarbonyl)-4-piperidinyl]acetamide hydrochloride, m.p. 164°–167° C., by reaction of benzyl 2-(R)-[(4-methoxybenzenesulfonyl) (4-picolyl)amino]-2-(4-piperidinyl)acetate dihydrochloride with N-methyl-N-phenylcarbamoyl chloride, and by carrying out the subsequent steps similarly as described above.

(m) Similarly prepared is N-hydroxy-2-(R)-[(4-methoxybenzenesulfonyl) (4-picolyl)amino]-2-[(N-(4-morpholino)-carbonyl)-4-piperidinyl]acetamide hydrochloride, m.p. >170° C. (dec), by reaction of benzyl 2-(R)-[(4-methoxybenzenesulfonyl) (4-picolyl)amino]-2-(4-piperidinyl) acetate dihydrochloride with morpholine-4-carbonyl chloride, and by carrying out the subsequent steps similarly as described above.

EXAMPLE 12

(a) Similarly prepared as described in example 1 is N-hydroxy-2-(R)-[(4-methoxybenzenesulfonyl) (4-picolyl)amino]-2-(4-N-propylpiperidinyl)acetamide dihydrochloride, m.p. >185° C. (dec). The required intermediate benzyl 2-(R)-[(4-methoxybenzenesulfonyl) (4-picolyl)amino]-2-(4-N-propylpiperidinyl)acetate is prepared as follows: Trough a solution of benzyl 2-(R)-[(4-methoxybenzenesulfonyl)amino]-2-(N-t-BOC-4-piperidinyl) acetate (1.69 g, 3.26 mmol) in methylene chloride (80 ml) cooled to 0° C. is bubbled hydrochloric acid for 5 minutes. The flask is sealed and the reaction mixture is stirred at room temperature for 1.5 hours. The solvent is removed in vacuo to provide benzyl 2-(R)-[(4-methoxybenzenesulfonyl)amino]-2-(4-piperidinyl) acetate hydrochloride. To a solution of benzyl 2-(R)-[(4-methoxybenzenesulfonyl)amino]-2-(4-piperidinyl) acetate hydrochloride (600 mg, 1.32 mmol) in dimethylformamide (10 ml) is added potassium carbonate (1.82 g, 13.2 mmol) and 1-iodopropane (0.13 ml, 1.39 mmol). The reaction mixture is stired at room temperature for 18 hours and 4-picolyl chloride hydrochloride (227 mg, 1.39 mmol) is added. The reaction mixture is stirred at room temperature for 8 hours. The reaction mixture is diluted with ethyl acetate and water, the organic layer is extracted, and the aqueous layer extracted with ethyl acetate. The combined organic layer is washed with aqueous lithium chloride, dried over sodium sulfate, and concentrated in vacuo. Purification by silica gel chromatography (10% to 20% methanol in ethyl acetate) provides benzyl 2-(R)-[(4-methoxybenzenesulfonyl) (4-picolyl)amino]-2-(4-N-propylpiperidinyl) acetate. The remainder of the synthesis is carried out similarly as described in example 1.

(b) Similarly prepared is N-hydroxy-2-(R)-[(4-methoxybenzenesulfonyl) (4-picolyl)amino]-2-[4-N-(3-phenylpropyl)-piperidinyl]acetamide dihydrochloride, m.p. >175° C. (dec), by using 1-bromo-3-phenyl-propane in the alkylation step, and by carrying out the subsequent steps similarly as described above.

EXAMPLE 13

Similarly prepared as illustrated in previous examples but starting from N-t-butoxy-carbonyl-3-pyrrolidineacetic acid are:

(a) N-hydroxy-2-(R)-[(4-methoxybenzenesulfonyl) (4-picolyl)-amino]-2-(N-ethoxycarbonyl-3-pyrrolidinyl)-acetamide hydrochloride.

(b) N-hydroxy-2-(R)-[(4-methoxybenzenesulfonyl) (4-picolyl)-amino]-2-(N-cyclohexyloxycarbonyl-3-pyrrolidinyl)-acetamide.

(c) N-hydroxy-2-(R)-[(4-methoxybenzenesulfonyl) (4-picolyl)-amino]-2-(N-methylsulfonyl-3-pyrrolidinyl)-acetamide hydrochloride.

(d) N-hydroxy-2-(R)-[(4-methoxybenzenesulfonyl) (4-picolyl)-amino]-2-(N-propionyl-3-pyrrolidinyl)-acetamide, m.p. 140° C.

(e) N-hydroxy-2-(R)-[(4-methoxybenzenesulfonyl) (4-picolyl)-amino]-2-(N-(2-phenylethoxycarbonyl)-3-pyrrolidinyl)-acetamide, m.p. 114° C.

(f) N-hydroxy-2-(R)-[(4-methoxybenzenesulfonyl) (4-picolyl)-amino]-2-(N-(4-tetrahydropyranyloxycarbonyl-3-pyrrolidinyl)-acetamide, m.p. 96°–98° C.

(g) N-hydroxy-2-(R)-[(4-methoxybenzenesulfonyl) (4-picolyl)-amino]-2-(N-benzenesulfonyl-3-pyrrolidinyl)-acetamide, m.p. 132° C.

(h) N-hydroxy-2-(R)-[(4-methoxybenzenesulfonyl) (4-picolyl)-amino]-2-(N-(2-cyclohexylethoxycarbonyl-3-pyrrolidinyl)-acetamide, m.p. 126° C.

(i) N-hydroxy-2(R)-[(4-methoxybenzenesulfonyl) (benzyl) amino]-2-(N-t-butoxycarbonyl-3-pyrrolidinyl)-acetamide, m.p. 120° C. dec.

EXAMPLE 14

Preparation of 3000 capsules each containing 25 mg of the active ingredient, for example, the compound of example 1(a):

| Active ingredient | 75.00 g |
|---|---|
| Lactose | 750.00 g |
| Avicel PH 102 (microcrystalline cellulose) | 300.00 g |
| Polyplasdone XL (polyvinylpyrrolidone) | 30.00 g |
| Purified water | q.s. |
| Magnesium stearate | 9.00 g |

The active ingredient is passed through a No. 30 hand screen.

The active ingredient, lactose, Avicel PH 102 and Polyplasdone XL are blended for 15 minutes in a mixer. The blend is granulated with sufficient water (about 500 mL), dried in an oven at 35° C. overnight, and passed through a No. 20 screen.

Magnesium stearate is passed through a No. 20 screen, added to the granulation mixture, and the mixture is blended for 5 minutes in a mixer. The blend is encapsulated in No. 0 hard gelatin capsules each containing an amount of the blend equivalent to 25 mg of the active ingredient.

What is claimed is:

1. A compound of the formula

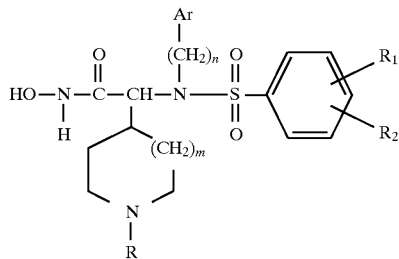

wherein R represents acyl derived from a carboxylic acid, from a carbonic acid or from a carbamic acid; or R represents (lower alkyl, aryl-lower alkyl or aryl)-sulfonyl, di-(aryl-lower alkyl, aryl or alkyl)-aminosulfonyl, or aryl-lower alkyl; Ar represents carbocyclic aryl, heterocyclic aryl or biaryl; $R_1$ and $R_2$ represent independently hydrogen, lower alkyl, lower alkoxy, halogen, hydroxy, acyloxy, lower alkoxy-lower alkoxy, trifluoromethyl or cyano; or $R_1$ and $R_2$ together on adjacent carbon atoms represent lower alkylenedioxy; m represents zero or one; n represents an integer from 1 to 5; a pharmaceutically acceptable prodrug derivative thereof; or a pharmaceutically acceptable salt thereof.

2. A compound according to claim 1 wherein m represents 1.

3. A compound according to claim 1 wherein the configuration of the asymmetric carbon atom of the α-aminohydroxamic acid moiety corresponds to that of a D-amino acid precursor and is assigned the (R)-configuration.

4. A compound according to claim 1 wherein R represents acyl derived from a carbonic acid.

5. A compound according to claim 4 of the formula

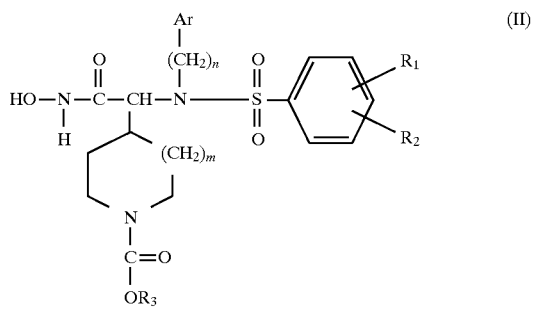

wherein Ar, $R_1$, $R_2$, m and n have meaning as defined in said claim; $R_3$ is lower alkyl; or $R_3$ is lower alkyl which is substituted by carbocyclic or heterocyclic aryl, biaryl, adamantyl, cycloalkyl, bicycloalkyl, alkoxy, phthalimido, 1,4-benzoxazin-3-onyl, benzoxazolonyl, amino, mono- or di-lower alkylamino, piperazino, N-lower alkylpiperazino, N-(carbocyclic or heterocyclic aryl-lower alkyl) piperazino, morpholino, thiomorpholino, piperidino, pyrrolidino, piperidinyl or N-lower alkylpiperidinyl, hexahydroazepino, hexahydroazepinyl or N-lower alkylhexahydroazepinyl, tetrahydroquinolinyl, tetrahydroisoquinolinyl or by lower alkoxy; a pharmaceutically acceptable prodrug derivative thereof; or a pharmaceutically acceptable salt thereof.

6. A compound according to claim 5 wherein m is one.

7. A compound of formula II according to claim 5 wherein Ar is pyridyl; m is one; n is one; $R_1$ and $R_2$ are hydrogen, lower alkoxy or halo; or $R_1$ and $R_2$ together on adjacent carbon atoms represent methylenedioxy; $R_3$ represents lower alkyl or lower alkyl substituted by quinolinyl, tetrahydroquinolinyl, pyridyl, carbocyclic aryl, indolyl or by phthalimido; a pharmaceutically acceptable prodrug derivative thereof; or a pharmaceutically acceptable salt thereof.

8. A compound according to claim 5 of formula II wherein Ar is 3- or 4-pyridyl; $R_1$ is lower alkoxy at the para position and $R_2$ is hydrogen; $R_3$ represents lower alkyl or lower alkyl substituted by carbocyclic aryl; a pharmaceutically acceptable prodrug derivative thereof; or a pharmaceutically acceptable salt thereof.

9. A compound according to claim 1 wherein R represents acyl derived from a carbamic acid.

10. A compound according to claim 9 of the formula III

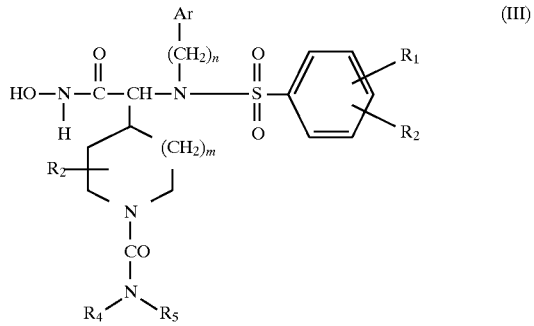

wherein Ar, $R_1$, $R_2$, m and n have meaning as defined in said claim; $R_4$ and $R_5$ independently represent hydrogen, lower alkyl, aryl, aryl-lower alkyl or acyl derived from a carboxylic acid; or $R_4$ and $R_5$ combined represent lower alkylene or lower alkylene interrupted by O, S, NH or by N-lower alkyl; a pharmaceutically acceptable prodrug derivative thereof; or a pharmaceutically acceptable salt thereof.

11. A compound according to claim 10 wherein m is one.

12. A compound according to claim 10 wherein Ar is pyridyl; m is one; n is one; $R_1$ is lower alkoxy; and $R_2$ is hydrogen.

13. A compound according to claim 12, wherein Ar is 3- or 4-pyridyl; and $R_1$ is at the para-position.

14. A compound according to claim 1 wherein R represents (lower alkyl, aryl-lower alkyl or aryl)-sulfonyl or di-(aryl-lower alkyl, aryl or alkyl)-aminosulfonyl.

15. A compound according to claim 14 of the formula

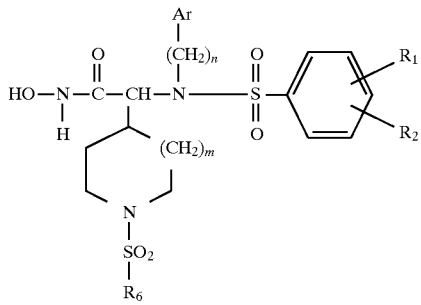

wherein Ar, $R_1$, $R_2$, m and n have meaning as defined in said claim and $R_6$ represents lower alkyl, cycloalkyl, aryl-lower alkyl, aryl, or di-(lower alkyl, aryl or aryl-lower alkyl)-amino.

16. A compound according to claim 15 wherein Ar is pyridyl; m is one; n is one; $R_1$ is lower alkoxy; and $R_2$ is hydrogen.

17. A compound according to claim 1 wherein R represents acyl derived from a carboxylic acid.

18. A compound according to claim 1 of the formula

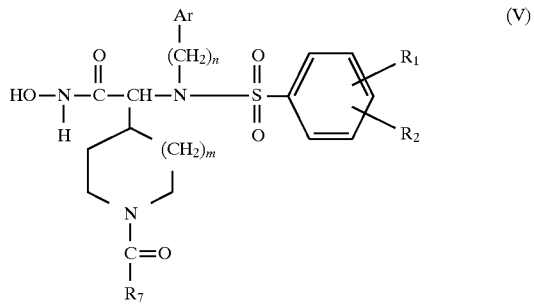

wherein Ar, $R_1$, $R_2$, m and n have meaning as defined in said claim and $R_7$ represents lower alkyl, aryl-lower alkyl, carbocyclic or heterocyclic aryl, cycloalkyl, cycloalkyl-lower alkyl, adamantyl, bicycloalkyl, or biaryl.

19. A compound according to claim 18 wherein Ar is pyridyl; m is one; n is one; $R_1$ is lower alkoxy; $R_2$ is hydrogen; and $R_7$ represents lower alkyl or aryl-lower alkyl.

20. A compound according to claim 5 which is N-hydroxy-2-(R)-[(4-methoxybenzenesulfonyl) (4-picolyl) amino]-2-[(N-(2-( 1-naphthyl)-ethoxycarbonyl))-4-piperidinyl]acetamide or a pharmaceutically acceptable salt thereof.

* * * * *